(12) United States Patent
Aferzon

(10) Patent No.: US 8,550,993 B2
(45) Date of Patent: *Oct. 8, 2013

(54) MINIMALLY INVASIVE SURGICAL RETRACTOR WITH AN EXPANDED FIELD OF VISION

(75) Inventor: Joseph Aferzon, Avon, CT (US)

(73) Assignee: International Spinal Innovations, LLC, West Hartford, CT (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/611,637

(22) Filed: Sep. 12, 2012

(65) Prior Publication Data

US 2013/0006059 A1    Jan. 3, 2013

Related U.S. Application Data

(63) Continuation of application No. 12/714,921, filed on Mar. 1, 2010, now Pat. No. 8,303,497.

(60) Provisional application No. 61/210,681, filed on Mar. 23, 2009.

(51) Int. Cl.
*A61B 1/06* (2006.01)
*A61B 1/32* (2006.01)

(52) U.S. Cl.
USPC .......................................... 600/212; 600/210

(58) Field of Classification Search
USPC ......... 600/212, 213, 219, 234, 201, 210, 224, 600/190, 196, 222, 184, 214, 208, 220
See application file for complete search history.

(56) References Cited

U.S. PATENT DOCUMENTS

| | | | | |
|---|---|---|---|---|
| 4,883,426 A | * | 11/1989 | Ferrer | 433/91 |
| 5,125,396 A | * | 6/1992 | Ray | 600/208 |
| 7,182,729 B2 | * | 2/2007 | Abdelgany et al. | 600/219 |
| 7,238,155 B2 | * | 7/2007 | Hu et al. | 600/232 |
| 8,303,497 B2 | * | 11/2012 | Aferzon | 600/212 |
| 2002/0099268 A1 | * | 7/2002 | Paul et al. | 600/201 |
| 2005/0159651 A1 | * | 7/2005 | Raymond et al. | 600/213 |
| 2006/0142643 A1 | * | 6/2006 | Parker | 600/219 |
| 2007/0208229 A1 | * | 9/2007 | Prusmack | 600/234 |

* cited by examiner

*Primary Examiner* — Pedro Philogene
(74) *Attorney, Agent, or Firm* — Hoffmann & Baron, LLP

(57) ABSTRACT

A surgical retractor includes a first component and a second component. The first component includes a first top structure and a conical outer wall. The first top structure has a first opening. The outer wall extends below the first top structure to form an ellipse-shaped second opening in communication with the first opening. The second component includes a second top structure and conical inner wall. The second top structure has a third. The inner wall extends below the second top structure to form an ellipse-shaped fourth opening in communication with the third opening. The second top structure of the second component is disposed at least partially inside the first top structure of the first component such that the second component is rotatably adjustable with respect to the first component.

29 Claims, 14 Drawing Sheets

MINIMALLY INVASIVE SURGICAL RETRACTOR WITH AN EXPANDED FIELD OF VISION

CROSS-REFERENCE TO RELATED APPLICATIONS

This application is a continuation of U.S. patent application Ser. No. 12/714,921 filed on Mar. 1, 2010, which claims priority to and benefit of U.S. Provisional Patent Application Ser. No. 61/210,681 filed on Mar. 23, 2009, both of which are incorporated herein by reference in their entireties.

BACKGROUND

1. Field of Technology

This application relates generally to surgical retractors. More specifically, this application is directed to a minimally invasive surgical retractor and method of minimally invasive retraction that expand the field of vision.

2. Brief Description of Related Art

A muscle sparing approach in spinal surgery reduces tissue trauma, decreases incision size and improves outcome of the surgery. An important component of the muscle sparing approach is the development of a working channel along a desired trajectory to a site within a patient that requires surgical correction. Various refractors addressing this need exist in the field.

Refractors range from simple tubular retractors to complex retractors that include plural blades connected by multiple joints. An advantage associated with a simple tubular refractor is that the retractor can be quickly applied and repositioned within the patient. Another advantage of the simple tube retractor is that the retractor can be made out of a plastic that is radiolucent, producing low artifact on an x-ray. A disadvantage of the simple retractor is its retraction space in comparison to the space required for its insertion.

The benefit of a complex retractor is that the retractor's blades can be collapsed for insertion and can be diverged by the multiple joints to improve retraction space once within the patient. Such collapsibility requires the complex retractor to be manufactured out of thin and stiff material which is invariably a metal alloy. The metal alloy it is not radiolucent. Moreover, the manipulation of each individual blade via the multiple joints is cumbersome.

SUMMARY

In accordance with an embodiment, a surgical retractor is provided. The surgical retractor includes a first component and a second component.

The first component includes a first top structure and a conical outer wall. The first top structure has a first opening. The conical outer wall extends below the first top structure to form an ellipse-shaped second opening in communication with the first opening. The second component includes a second top structure and a conical inner wall. The second top structure has a third opening. The conical inner wall extends below the second top structure to form an ellipse-shaped fourth opening in communication with the third opening.

Moreover, the second top structure of the second component is disposed at least partially inside the first top structure of the first component and is rotatably adjustable with respect to the first component from a first rotational configuration to a second rotational configuration in which the ellipse-shaped second opening and the ellipse-shaped fourth opening define a combined opening in communication with the third opening to provide an expanded field of vision.

In accordance with another embodiment, a surgical retractor system is provided. The surgical retractor system includes a surgical retractor and a driver tool. The surgical retractor includes a first component and a second component.

The first component includes a first top structure and a conical outer wall. The first top structure has a first opening. The conical outer wall extends below the first top structure to form an ellipse-shaped second opening in communication with the first opening. The second component includes a second top structure and a conical inner wall. The second top structure has a third opening. The conical inner wall extends below the second top structure to form an ellipse-shaped fourth opening in communication with the third opening.

Moreover, the second top structure of the second component is disposed at least partially inside the first top structure of the first component such that the second component is rotatably adjustable with respect to the first component. The driver tool is configured to engage the second top structure of the second component and to rotate the second component with respect to the first component from a first rotational configuration to a second rotational configuration in which the ellipse-shaped second opening and the ellipse-shaped fourth opening define a combined opening that is in communication with the third opening to provide an expanded field of vision.

In accordance with a further embodiment, a method of retracting is provided. The method includes inserting a surgical refractor in an incision of a patient.

The surgical retractor includes a first component and a second component. The first component has a first top structure that includes a first opening, and a conical outer wall extending below first top structure to form an ellipse-shaped second opening in communication with the first opening. The second component has a second top structure that includes a third opening, and a conical inner wall extending below the second top structure to form an ellipse-shaped fourth opening in communication with the third opening. The second top structure of the second component is disposed at least partially inside the first top structure of the first component in first rotational configuration.

The method further includes rotating the second component with respect to the first component from the first rotational configuration to a second rotational configuration in which the ellipse-shaped second opening and the ellipse-shaped fourth opening define a combined opening that is in communication with the third opening to provide an expanded field of vision.

For a more thorough understanding of the present invention, reference is made to the following description, taken in conjunction with the accompanying drawings, and its scope will be pointed out in the appended claims.

BRIEF DESCRIPTION OF THE DRAWINGS

Some embodiments are illustrated by way of example and not limitation in the figures of the accompanying drawings in which.

DETAILED DESCRIPTION

A minimally invasive surgical retractor and a method of minimally invasive retraction that expand the field of vision are disclosed. In the following description, for the purposes of explanation, numerous specific details are set forth in order to provide a thorough understanding of example embodiments. It will be evident, however, to one skilled in the art, that an example embodiment can be practiced without all of the disclosed specific details.

Figure 1:
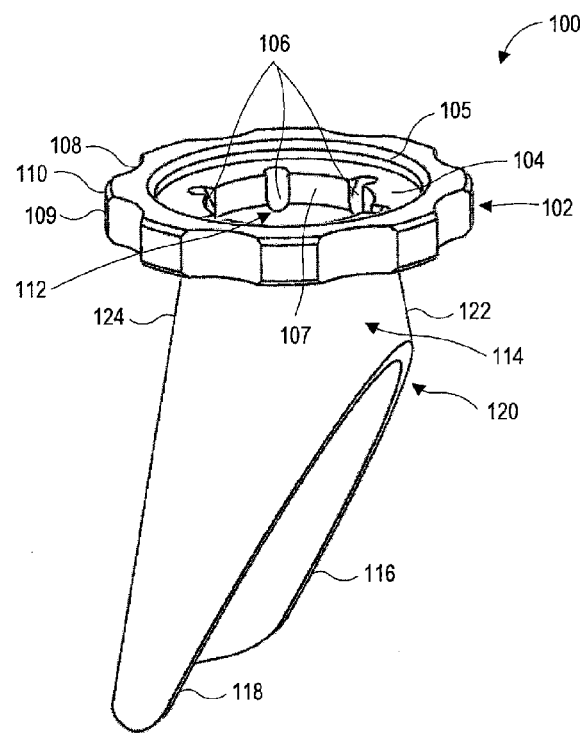
FIG. 1 illustrates a perspective view of an example outer component of a minimally invasive surgical retractor with expanded field of vision according to a first embodiment.
Figure 6:
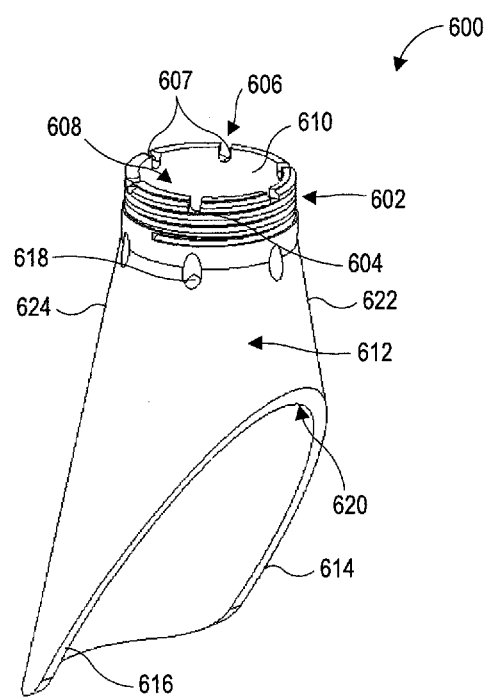
FIG. 6 illustrates a perspective view of an example inner component of the minimally invasive surgical retractor with expanded field of vision, according to the first embodiment.

FIG. 1 illustrates a perspective view of an example outer component 100 of a minimally invasive surgical retractor with expanded field of vision according to a first embodiment. The minimally invasive surgical refractor and its operation are illustrated in and described with reference to FIGS. 17-22 below. The outer component 100 is configured to mate adjustably in a first rotational configuration (e.g., closed configuration) with respect to an example inner component (illustrated in FIG. 6). The outer component 100 is also configured to rotate adjustably to a second rotational configuration (e.g., open configuration) with respect to the inner component, and to secure rigidly in at least one of the rotational configurations, such as via a top nut (illustrated in FIG. 13). Other securing mechanisms can be employed to secure the outer component 100 with respect to the inner component of FIG. 6. In various embodiments, one or more additional rotational configurations of the outer component 100 with respect to the inner component of FIG. 6 are possible. The outer component 100 is further configured to mate in one or more rotational configurations with the support arm (illustrated in FIG. 11).

The outer component 100 includes an example top ring structure 102 and an example bottom cone-shaped (conical) outer wall 114. The ring structure 102 is configured to facilitate the handling and manipulation of the outer component 100 and the assembled retractor, as illustrated in FIGS. 17-22. A top surface of the ring structure defines a plane. In one embodiment, the plane can be substantially horizontal. The ring structure 102 includes a recessed seat member 104 and a retaining grip member 109. The recessed seat member 104 includes a bevelled edge wall 105 and is configured to mate in a planar configuration with (or to receive) a support arm (illustrated in FIG. 11) and further to mate in a transverse configuration with (or to receive) the inner component (illustrated in FIG. 6).

The recessed seat member 104 includes a central opening 112 and a plurality of peripheral light openings 106. The central opening 112 is bounded by a cylindrically-shaped (cylindrical) inner wall 107. The peripheral light openings 106 are disposed about the cylindrical inner wall 107 and are angled with respect to the surface of the recessed seat member 104, extending through the recessed seat member 104 towards the central opening 112 of the recessed seat member 104 such that the peripheral light openings 106 are in communication with the central opening 112. As will be described in greater detail below, at least one of the peripheral light openings 106 is disposed and angled to communicate with at least one peripheral light opening of the inner component illustrated in FIG. 6, in various rotational configurations. In one embodiment, the peripheral light openings 106 are equidistantly disposed about the inner wall 107 and extend through the surface of the inner wall 107. In alternate embodiments, the peripheral light openings 106 may be disposed at various locations about the cylindrical inner wall 107. Although six (6) peripheral light openings 106 are illustrated with respect to the recessed seat member 104, more or fewer peripheral light openings 106 may be provided as desired. In some embodiments, the peripheral light openings 106 may be omitted, as will be described hereinbelow.

Figure 11:
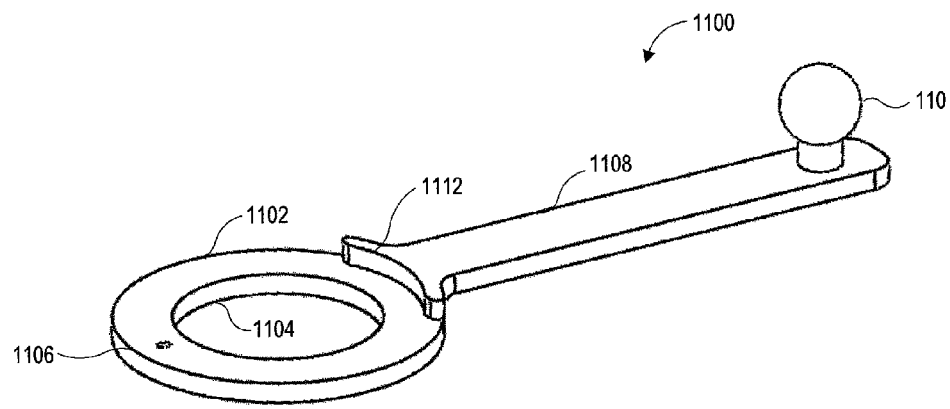
FIG. 11 illustrates a perspective view of an example support arm of the minimally invasive surgical retractor with expanded field of vision according to the first embodiment.

The retaining grip member 109 is configured to retain the minimally invasive surgical retractor outside an incision during surgery and further configured to provide the ability to grasp the outer component 100 for insertion and extraction of the minimally invasive surgical retractor with respect to the incision and for rotation of the outer component 100 with respect the inner component (illustrated in FIG. 6) and the support arm (illustrated in FIG. 11). The retaining grip member 109 includes alternating depressions 108 and protrusions 110 to facilitate grasping, holding and rotating. In some embodiments, the retaining grip member 109 is configured to be wider than the narrowest part of the conical outer wall 114 to retain the minimally invasive surgical retractor outside the body during surgery.

The conical outer wall 114 is configured to provide for minimally invasive insertion while expanding the field of vision, as will be described in greater detail below. The conical outer wall 114 extends down and away from the ring structure 102, forming an acute angle (e.g., angle <90 degrees) with respect to the plane of the ring structure 102. The conical wall 114 has a first side 122 and a second side 124, and includes an oval-shaped (or ellipse-shaped) arch 120 extending from the first side 122 to the second side 124. The arch 120 includes curvilinear or arcuate walls 116, 118. The conical outer wall 114 and its formation will be described in greater detail with reference to FIG. 3.

The outer component 100 can be made of a radiolucent plastic material (e.g., producing low artefact on an x-ray), another material, or a combination of materials. For example, the following materials and combinations thereof can be used: plastic, acrylic, polyether-ether-ketone (e.g., PEEK), carbon fiber, and metal. Other medically/surgically appropriate materials that have not been enumerated herein can also be used. In some embodiments, the entire outer component 100 can be opaque. In alternate embodiments, one or more portions of the outer component 100 can be translucent to transmit light. For example, the top ring structure 102 can be opaque, while the conical outer wall 114 can be translucent. As another example, the recessed seat member 104 (or an inner portion thereof about the inner wall 107) and the conical outer wall 114 can be translucent, while the retaining grip member 109 can be opaque. Where the recessed seat member 104 (or a portion thereof) is translucent, the peripheral light openings 106 can be omitted. This is because the light can be transmitted through at least the translucent portion of the recessed seat member 104 instead of the peripheral light openings 106.

Figure 2:
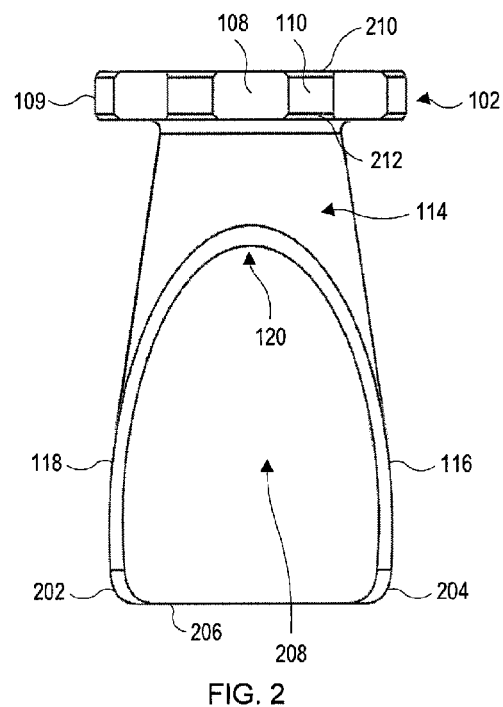
FIG. 2 illustrates a front view of the example outer component illustrated in FIG. 1.

FIG. 2 illustrates a front view of the example outer component 100 illustrated in FIG. 1. As illustrated in FIG. 2, the arch 120 includes arcuate walls 116, 118, which taper toward an arcuate bottom 206 of the conical outer wall 114. The arcuate bottom 206 is illustrated in and described with reference to FIG. 5. In one embodiment, the taper is arcuate to provide a smooth transition between the arcuate walls 116, 118 of the arch 120 and the bottom 206 of the conical outer wall 114. In some embodiments, the arcuate walls 116, 118 of the arch 120 connect to the arcuate bottom 206 via taper section 202, 204, forming a smooth transition between the arch 120 and the bottom 206. The arch 120 and the bottom 206 form an opening 208 of the outer component 100 through which the inner component (illustrated in FIG. 6) is received. As further illustrated in FIG. 2, each of the protrusions 110 in the retaining grip member 109 includes a top bevelled edge 210 and a bottom bevelled edge 212.

Figure 3:
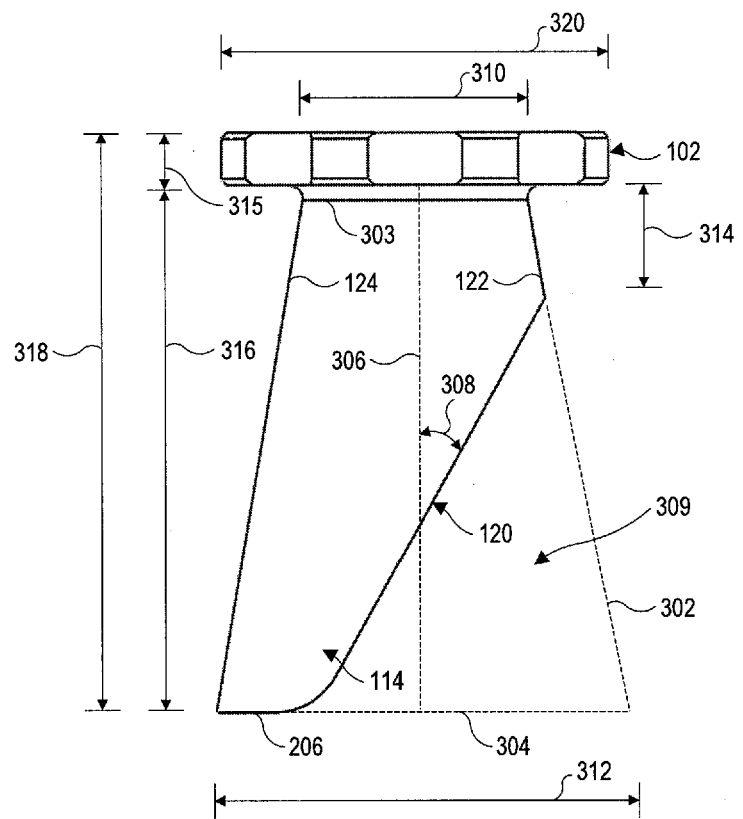
FIG. 3 illustrates a side view of the example outer component illustrated in FIG. 1.

FIG. 3 illustrates a side view of the example outer component 100 illustrated in FIG. 1. The overall outer component 100 has a height 318 and a width 320. The top ring structure 102 has a height 315 and the conical outer wall 114 has a height 316. The conical outer wall 114 is formed from a truncated cone 302. More specifically, the conical outer wall 114 is defined by a central portion of the cone 302 delimited by a first plane 303 of the cone 302 that is perpendicular to the axis 306 of the cone 302, and a second plane 304 that is non-coplanar with the first plane 303 and that is also perpendicular to the axis 306. The first plane 303 is offset below the vertex (not shown) (e.g., non-coplanar with the vertex) such that a circle defined by the first plane 303 has a diameter 310. The second plane 304 is offset below the first plane 303 such that a circle defined by the second plane 304 has a diameter 312. The second plane 304 can be said to define a circular base 304 of the cone 302. These terms are used interchangeably herein.

The conical outer wall 114 is further formed by removing a section 309 from the truncated cone 302. More specifically, the section 309 that is removed is defined by an offset length 314 from the first side 122 below the first plane 303 of the cone 302 and angled down at an acute angle 308 with respect to the axis 306 toward about the second plane 304 of the opposite second side 124 of the cone 302. The relationship amongst the offset length 314, angle 308 and height 316 can be adjusted to define the removed section 309, and in turn to define the arcuate bottom 206 having a shape that forms a portion of the base 304 of the cone 302. In some embodiments, the arcuate bottom 206 is greater than zero (0) degrees and less than 180 degrees of the base 304 of the cone 302 (e.g., about 120 degrees to about 150 degrees). In other embodiments, the arcuate bottom 206 is greater than 180 degrees and less than 360 degrees of the base 304 of the cone 302. Accordingly, the arcuate bottom 206 forms a portion of the circular base 304 of the cone 302.

An outer diameter 320 of the retaining grip member 109 can be approximately the same as the diameter 312 of the circular base 304 of the truncated cone 302. In alternate embodiments, the respective diameters can be different as desired.

Figure 4:
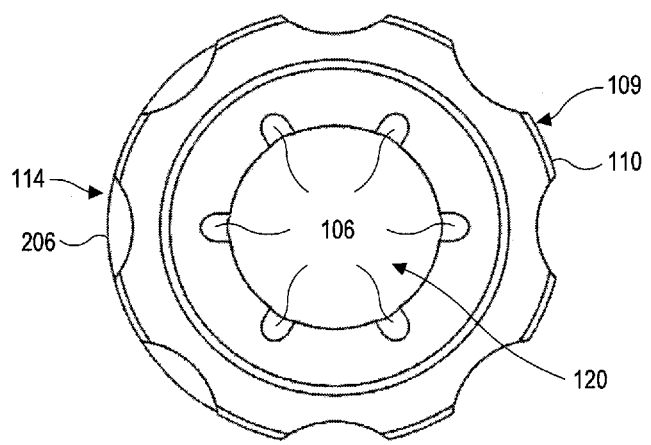
FIG. 4 illustrates a top view of the example outer component illustrated in FIG. 1.
Figure 5:
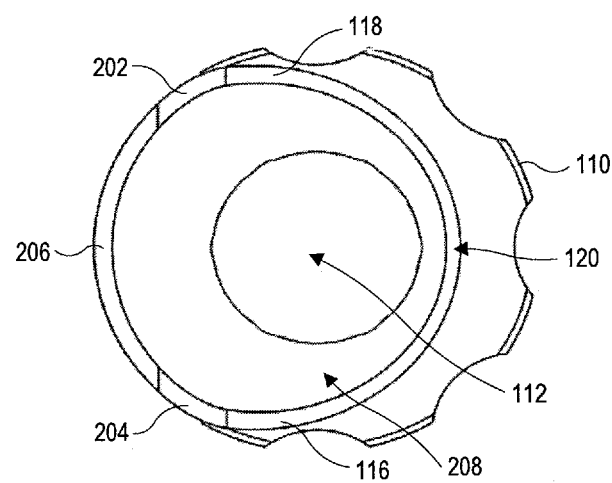
FIG. 5 illustrates a bottom view of the example outer component illustrated in FIG. 1.

FIG. 4 illustrates a top view of the example outer component 100 illustrated in FIG. 1. The arcuate bottom 206 of the conical outer wall 114 can be coincident with a shape that bounds the outer periphery (e.g., outside bounds of the protrusions 110) of the retaining grip member 109, as illustrated in FIG. 4 and FIG. 5, which is described below. In other embodiments, the arcuate bottom 206 of the conical outer wall 114 can be non-coincident with the shape that bounds the outer periphery of the retaining grip member 109. As illustrated in FIG. 4, the peripheral light openings 106 are disposed equidistantly about the inner wall 107 and extend towards the central opening 112 of the recessed seat member 104. In other embodiments, more or fewer peripheral light openings 106 can be disposed at various locations about the cylindrical inner wall 107, or the peripheral light openings 106 can be omitted entirely.

FIG. 5 illustrates a bottom view of the example outer component 100 illustrated in FIG. 1. The arcuate bottom 206 of the conical outer wall 114 is coincident with about a ⅓ (e.g., 120 degrees to about 150 degrees) of the shape that bounds the outer periphery of the retaining grip member 109. As further illustrated in FIG. 5, the arch 120 of the conical outer wall 114 is non-coincident with the shape that bounds the retaining grip member 109. In various embodiments, depending on the section 309 that is removed from the cone 302 (as illustrated in FIG. 3), more or less of the arcuate bottom 206 of the conical outer wall 114 can be coincident with the with the shape that bounds retaining grip member 109. Depending on particular surgical requirements, the arcuate bottom 206 can be configured to have a minimally invasive shape while also providing an expanded field of retraction. As further illustrated in FIG. 5, the central opening 112 is open to and is in communication with opening 208 formed by the conical outer wall 114. Accordingly, the peripheral light openings 106 are in communication with the openings 112 and 208.

FIG. 6 illustrates a perspective view of an example inner component 600 of the minimally invasive surgical retractor with expanded field of vision according to the first embodiment. As described above with reference to FIG. 1, the minimally invasive surgical retractor and its operation are illustrated in and described with reference to FIGS. 17-22 below. The inner component 600 is configured to be disposed adjustably in a first rotational configuration (e.g., closed configuration) with respect to the example outer component 100 of FIG. 1. The inner component 600 is further configured to rotate adjustably to a second rotational configuration (e.g., open configuration) with respect to the outer component 100, and to secure rigidly in at least one of the rotational configurations, such as via the top nut illustrated in FIG. 13. Other securing mechanisms can be employed to secure the inner component 600 with respect to the outer component 100. In various embodiments, one or more additional rotational configurations of the inner component 600 with respect to the outer component 100 are possible. The inner component 600 is further configured to mate in one or more rotational configurations with the support arm illustrated in FIG. 11.

The inner component 600 includes an example top screw structure 602 and an example bottom cone-shaped (conical) inner wall 612. The top screw structure 602 of the inner component 600 is configured to be received or disposed at least partially inside the ring structure 102 of the outer component 100 of FIG. 1, e.g., via openings 208 and 112, such that the inner component 600 can be rotatably adjustable from the first rotational configuration with respect to the outer component 100 to the second rotational configuration with respect to the outer component 100. The top screw structure 602 is also configured to mate in a rotational configuration with (or to receive) the support arm illustrated in FIG. 11. A top surface of the screw structure 602 defines a plane. In one embodiment, the pane can be substantially horizontal.

The top screw structure 602 of the inner component 600 includes a thread 604, a receiving device 606 and a central opening 608. In one embodiment, the receiving device 606 includes a plurality of notches 607 configured to engage a driver tool as described in greater detail below with reference to FIG. 14. The central opening 608 is bounded by a cylindrically-shaped (cylindrical) inner wall 610.

Figure 13:
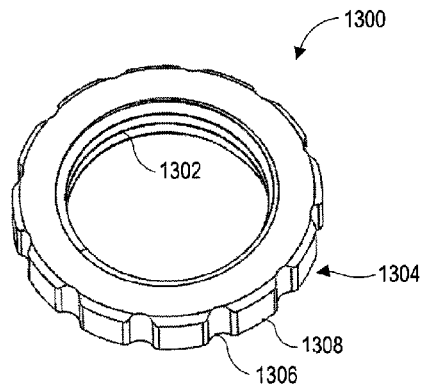
FIG. 13 illustrates a perspective view of a nut of the minimally invasive surgical retractor with expanded field of vision according to the first embodiment.

The thread 604 is configured to receive the top nut of FIG. 13 to allow the inner component 600 to be rigidly secured with respect to the outer component 100, as well as with respect to the support arm. The top nut of FIG. 13 can be loosed and tightened to facilitate rotational adjustability and rigidity, respectively, of the inner component 600 with respect to the outer component 100 and with respect to the support art.

Figure 14:
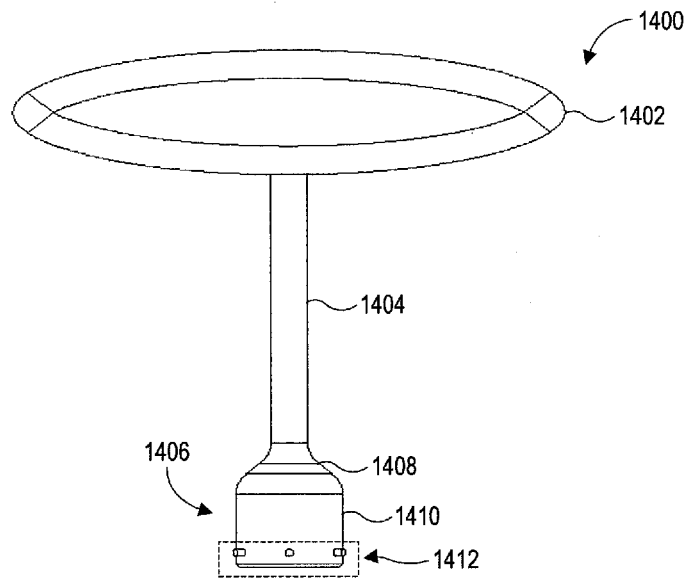
FIG. 14 illustrates a side view of a driver tool configured to engage the inner component illustrated in FIG. 6.

The receiving device 606 (e.g., notches 607) is disposed in the top of the screw structure 602 and is configured to engage a connector device (e.g., protrusions) of the driver tool illustrated in FIG. 14, providing for rotational adjustability of the inner component 600 with respect to the outer component 100 and the support arm of FIG. 11. In one embodiment, the notches 607 are equidistantly disposed about the screw structure 602 and extend transversely to the thread 604. In alternate embodiments, the notches 607 can be disposed at various locations about the screw structure 602. Although six (6) notches 607 are illustrated, more or fewer notches may be provided as desired.

The example conical inner wall 612 of the inner component 600 is configured to provide for minimally invasive insertion while expanding the field of vision. The conical inner wall 612 extends down and away from the screw structure 602, forming an acute angle (e.g., angle <90 degrees) with respect to the plane of the screw structure 602. The conical inner wall 612 has a first side 622 and a second side 624, and includes an oval-shaped or ellipse-shaped arch 620 extending from the fist side 622 to the second side 624 and a plurality of peripheral light openings 618. The arch 120 includes curvilinear or arcuate walls 614, 616. The conical inner wall 612 and its formation will be described in greater detail with reference to FIG. 8.

The example conical inner wall 612 includes peripheral light openings 618 that are disposed about the conical inner wall 612 and extend through the conical inner wall 612 to the interior of the inner component 600 at an acute angle with respect to the plane of the screw structure 602 described above. The angle of the peripheral light openings 618 with respect to the plane of the screw structure 602 can be similar or different than the angle of the peripheral light openings 106 with respect to the plane or surface of the recessed seat member 104 illustrated in FIG. 1. In one embodiment, the peripheral light openings 618 are equidistantly disposed about the conical inner wall 612. In alternate embodiments, the peripheral light openings 618 can be disposed at various locations about the conical inner wall 612. Although six (6) peripheral light openings 106 are illustrated, more or fewer peripheral light openings 618 can be provided as desired. In the different embodiments, at least one peripheral light opening 618 of FIG. 6 is in communication with at least one peripheral light opening 106 of FIG. 1, in one or more rotational configurations of the inner component 600 with respect to the outer component 100. In some alternate embodiments, the peripheral light openings 618 can be omitted, as will be described hereinbelow.

The inner component 600 can be made of a radiolucent plastic material, (e.g., producing low artefact on an x-ray), another material, or a combination or materials. For example, the following materials and combinations thereof can be used: plastic, acrylic, polyether-ether-ketone (e.g., PEEK), carbon fiber, and metal. Other medically/surgically appropriate materials that have not been enumerated herein can also be used. In some embodiments, the entire inner component 100 can be opaque. In alternate embodiments, one or more portions of the inner component 600 can be translucent to transmit light. For example, the screw structure 602 can be opaque, while the conical inner wall 612 (or portion thereof) can be translucent. Because the conical inner wall 612 (or a portion thereof) is translucent, the peripheral light openings 618 can be omitted. This is because the light can be transmitted through at least the translucent portion of the conical inner wall 612.

In some alternate embodiments, the top screw structure 602 can be substituted and/or improved with an additional mechanism configured to provide for rotational adjustment/engagement of the inner component 600 with respect to the outer component 100, as well as with respect to the support arm of FIG. 11. For example, the top screw structure 602 can be provided with at least one slot or channel transverse to the thread 604 (e.g., transverse slot) that can enable the top structure 602 to be squeezed, reducing its diameter to be fractionally smaller than the diameter of the opening 112 of ring structure 102, such that the top structure 602 can be disposed at least partially within the ring structure 102. The inner component 600 can be rotationally configured with respect to the outer component 100 by overcoming the friction either through reducing the diameter of the top structure 602 or using a tool that can engage the slots and can provide sufficient torsion to overcome the friction.

In some embodiments, multiple transverse channels disposed about the screw structure can be provided. Once the top structure 602 is released, its diameter can approximate the diameter of the opening 112 such that the inner component 600 can be engaged by friction fitting in the selected rotational configuration with respect to the outer component 100. Similarly, the support arm of FIG. 11 and the nut of FIG. 13 can also be disposed and engaged in a similar fashion. Once the nut of FIG. 13 is engaged, it can be rotated with respect to the thread 604 of the top structure 604 to provide tighter engagement between the inner component 100, outer component 600, support arm of FIG. 11, and nut of FIG. 13.

Figure 7:
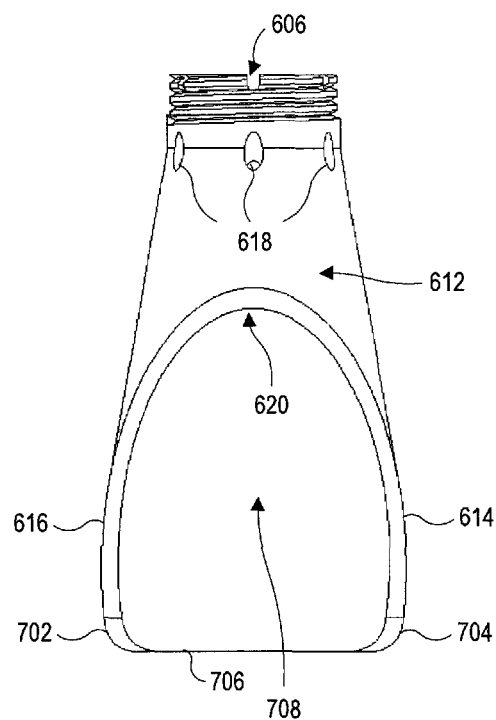
FIG. 7 illustrates a front view of the example inner component illustrated in FIG. 6.

FIG. 7 illustrates a front view of the example inner component 600 illustrated in FIG. 6. As illustrated in FIG. 6, the arch 620 includes arcuate walls 614, 616, which taper toward an arcuate bottom 706 of the conical inner wall 612. In one embodiment, the taper is curvilinear or arcuate to provide a smooth transition between the arcuate walls 614, 616 of the arch 620 and the bottom 706 of the conical inner wall 612. In one embodiment, the arcuate walls 614, 616 of the arch 620 connect to the arcuate bottom 706 via taper section 702, 704, forming a smooth transition between the arch 620 and the bottom 706. The arch 620 and the bottom 706 form an opening 708 of the inner component 600. As further illustrated in FIG. 7, the peripheral light opening 618 are in communication with the opening 708.

Figure 8:
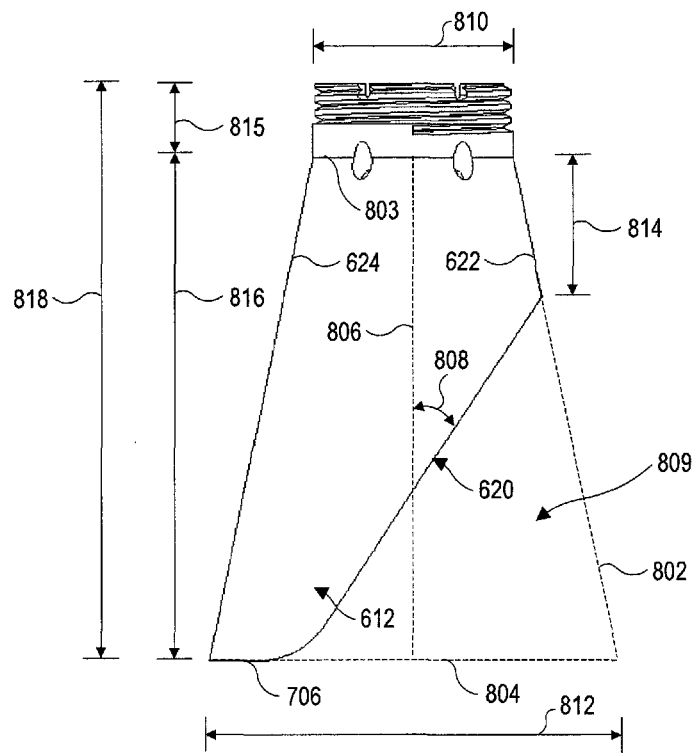
FIG. 8 illustrates a side view of the example inner component illustrated in FIG. 6.

FIG. 8 illustrates a side view of the example inner component 600 illustrated in FIG. 6. The overall inner component 600 has a height 818. The screw structure 602 has a height 815 and the conical inner wall 612 has height 816. The conical inner wall 612 is formed from a truncated cone 802. More specifically, the conical inner wall 612 is defined by a central portion of the cone 802 delimited by a first plane 803 of the cone 802 that is perpendicular to the axis 806 of the cone 802, and a second plane 804 that is non-coplanar with the first plane 803 and that is also perpendicular to the axis 806. The first plane 803 is offset below the vertex (not shown) (e.g., non-coplanar with the vertex) such that a circle defined by the first plane has a diameter 810. The second plane 804 is offset below the first plane 803 such that a circle defined by the second plane 804 has a diameter 812. The second plane 804 can be said to define a circular base 804 of the cone 802. These terms are used interchangeably herein.

The conical inner wall 612 is further formed by removing a section 809 from the cone 302. More specifically, the section 809 that is removed is defined by an offset length 814 from the first side 622 below the first plane 803 of the cone 802 and angled down at an acute angle 808 with respect to the axis 806 toward about the second plane 804 of the opposite second side 624 of the cone 802. The removed section 809 can be similar to or different than the removed section 309 of FIG. 3. The relationship amongst the offset length 814, angle 808 and height 816 can be adjusted to define removed section 809, and in turn to define the arcuate bottom 706 having a shape that forms a portion of the base 804 of the cone 802. In some embodiments, the arcuate bottom 706) is greater than zero (0) degrees and less than 180 degrees of the base 804 of the cone 802 (e.g., about 120 degrees to about 150 degrees). In other embodiments, the arcuate bottom 706 is greater than 180 degrees and less than 360 degrees of the base 804 of the cone 802. Accordingly, the arcuate bottom 706 forms a portion of the circular base 804 of the cone 802. In various embodiments, the arcuate bottom 706 can be similar to or different than the arcuate bottom 206 of FIG. 3.

Figure 9:
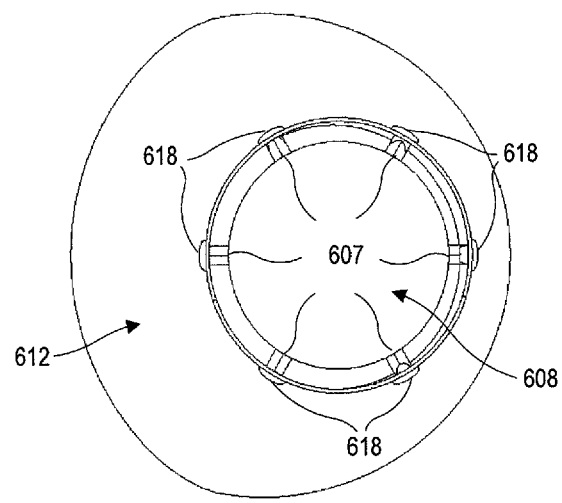
FIG. 9 illustrates a top view of the example inner component illustrated in FIG. 6.

FIG. 9 illustrates a top view of the example inner component 600 illustrated in FIG. 6. As illustrated in FIG. 9, the notches 607 of receiving device 606 are equidistantly disposed in the top of the screw structure 602. In various embodiments, the number of the notches 607 can vary and the notches 607 can be disposed at various locations about the screw structure 602. As further illustrated in FIG. 9, the peripheral light openings 618 are equidistantly disposed about the conical inner wall 612 and are in communication with opening 608, which in turn is in communication with opening 708, as shown in greater detail in FIG. 10. In various embodiments, at least one peripheral light opening 618 communicates with at least one peripheral light opening 106 of FIG. 1, in one or more rotational configurations of the inner component 600 with respect to the outer component 100.

Figure 10:
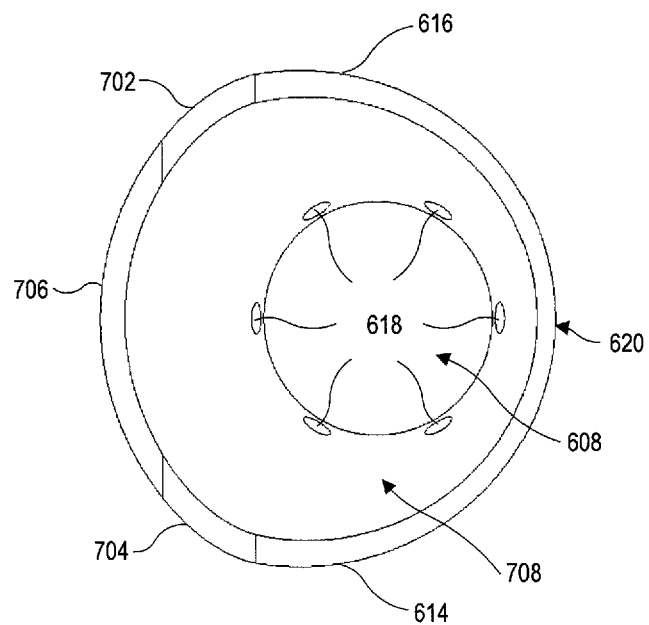
FIG. 10 illustrates a bottom view of the example inner component illustrated in FIG. 6.

FIG. 10 illustrates a bottom view of the example inner component 600 illustrated in FIG. 6. The arcuate bottom 706 of the conical inner wall 612 makes up about ⅓ (e.g., 120 degrees to about 150 degrees) of the base 804 of the cone 802 illustrated in FIG. 8. In various embodiments, depending on the section 809 that is removed from the cone 802 (as illustrated in FIG. 8), the arcuate bottom 706 can make up more or less of the base 804 of the cone 802. Depending on particular surgical requirements, the arcuate bottom 706 can be configured to have a minimally invasive shape while also providing an expanded field of retraction. As further illustrated in FIG. 10, the peripheral light openings 618 are in communication with opening 708, which in turn is open to and in communication with opening 608.

FIG. 11 illustrates a perspective view of an example support arm 1100 of the minimally invasive surgical retractor with expanded field of vision according to the first embodiment. The support arm 1100 is configured to mount or rigidly secure the minimally invasive surgical retractor to an external support structure of an operating table (not shown). Once the surgical retractor is in a desired position, multiple joints of the external support structure are locked to fixate the surgical retractor position and orientation in relation to the operating table and the patient. The example support arm 1100 includes a retractor attachment device 1102, a handle 1108 and a support attachment device 1110. Furthermore, the retractor attachment device 1102 includes apertures 1104, 1106.

The retractor attachment device 1102 is configured to mate in one or more rotational configurations with respect to the outer component 100 and inner component 600 of FIGS. 1 and 6, respectively. More specifically, the retractor attachment device 1102 is configured to receive the top screw structure 602 of the inner component 600 through the aperture 1104 and further configured to be seated in the recessed seat member 104 of the outer component 100. Once received as described above, the outer component 100, inner component 600 and support arm 1100 are rotationally adjustable to various rotational configurations with respect to one another. In some embodiments described hereinabove, the top structure 602 can friction fit the aperture 1104 to rigidly secure the support arm 1100 in a certain rotational configuration with the outer component 100. In such embodiments, the aperture 1106 can be omitted. In other embodiments, the aperture 1106 can receive a screw (not shown) to rigidly secure the support arm 1100 in a certain rotational configuration to the outer component 100.

The handle 1108 extends from the retractor attachment device 1102 and is configured to allow positioning of the retractor attachment device 1102 in the recessed seat member 104 of the outer component 100 in one or more rotational configurations with respect to the outer component 100 and inner component 600 of FIGS. 1 and 6, respectively. Furthermore, the handle 1108 includes an upright lip 1112 disposed about at least a portion of the periphery of the attachment device 1102. The lip 1112 is configured to impart strength at an intersection of the attachment device 1102 and the handle 1108, as the attachment device 1102 is seated in the recessed seat member 104, while allowing a nut described with reference to FIG. 13 to be disposed in planar configuration with the attachment device 1102.

The support attachment device 1110 extends from a terminal end of the handle 1108 and is configured to or secure to the external support structure described above. In one embodiment, the support attachment device 1110 can be a ball that is received in a socket of the external support structure. The ball and socket joint can be locked in desired position to fixate the surgical retractor as described above.

Figure 12:
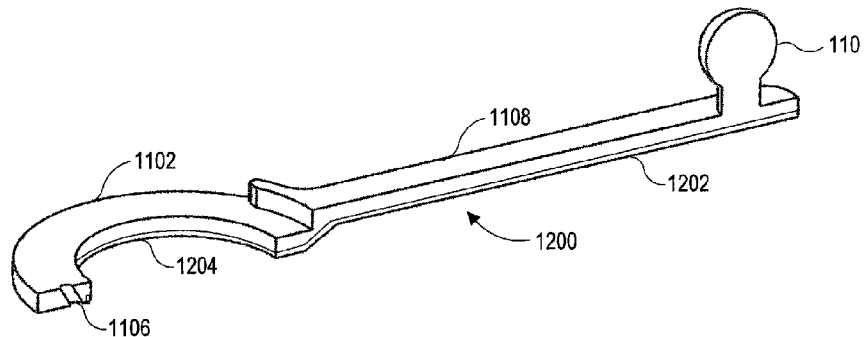
FIG. 12 illustrates a cross-sectional view of the example support arm illustrated in FIG. 11.

FIG. 12 illustrates a cross-sectional view of the example support arm 1100 illustrated in FIG. 11. As illustrated in FIG. 12, the aperture 1106 extends through the attachment device 1102. In one embodiment, the aperture 1106 can extend through the attachment device 1102 at an acute angle with respect to a plane defined by a top surface of the attachment device 1102. In another embodiment, the aperture 1106 can extend substantially transversely to the plane defined by a top surface of the 1102.

The example support arm 1100 includes a light emitting device 1200. The light emitting device 1200 can be a fiber optic cable or fiber connected to a light source (not shown). A first portion 1202 of the light emitting device 1200 can be covered or embedded in the handle 1108 to mitigate emission of light, while a second portion 1204 of the light emitting device 1200 can be exposed to emit light into the expanded field of vision defined by the components 100, 600, as will be described in greater detail below with reference to FIGS. 20-22. The second portion 1204 extends around at least a portion of the aperture 1104 and is configured to communicate light through the peripheral light openings 106 of the outer component 100 or through at least a portion of the recessed seat member 104 in embodiments where peripheral light openings 106 are omitted and the portion of the recessed seat member 104 is translucent.

FIG. 13 illustrates a perspective view of a nut 1300 of the minimally invasive surgical retractor with expanded field of vision according to the first embodiment. The nut 1300 is configured to secure the outer component 100, inner component 600 and support arm 1100 in one or more suitable rotational configurations. The nut 1300 includes an inner thread 1302, and a grip member 1304. The inner thread is configured to mate with the thread 604 of the inner component 600. Accordingly, when the nut 1300 is tightened with respect to the inner component 600, the conical inner wall 612 of inner component 600 is constricted by the conical outer wall 114 of the outer component 100 and the support arm 1100 is pressed into the recessed seat 104 of the outer component 100 in suitable rotational configurations. The grip member 1304 is configured to provide the ability to grasp the nut 1300 in order to fixate the outer component 100 with respect the inner component 600 and the support arm 1100. The grip member 1304 includes alternating depressions 1306 and protrusions 1308 to facilitate grasping, holding and rotating the nut 1300.

In alternate embodiments where the inner component 600 includes at least one transverse slot, the nut 1300 can be omitted entirely or can be used to provide additional fixation of the inner component 600 in a rotational configuration with respect to the outer component 100 and with respect to the support arm. The nut 1100 can further include a twist down mechanism (not shown) to fixate the components 100, 600 and the support arm 1100 together.

FIG. 14 illustrates a side view of a driver tool 1400 configured to engage the inner component 600 illustrated in FIG. 6. The driver tool 1400 is configured to adjust rotational configuration of the inner component 600 with respect to the outer component 100. The driver tool 1400 includes a handle 1402, body 1404 and head 1406.

The handle 1402 is sized and dimensioned to facilitate the user in grasping the driver tool 1400 and in providing sufficient force to rotate inner component 600 with respect to the outer component 100. The handle 1402 includes arcuate top, bottom, left and right surfaces, as will be described below in greater detail with regard to FIGS. 15 and 16.

The body 1404 connects the handle 1402 to the head 1406. The body 1404 can be sized and dimensioned as desired for different applications. In one embodiment the body 1404 is generally cylindrical.

The head 1406 includes a taper section 1408, terminal body 1410 and connector device 1412. The taper section 1408 includes a plurality conical sections that taper the body 1404 to the terminal body 1410 of the head 1406. In one embodiment, the terminal body 1410 is configured to be received partially into the central opening 608 to removably engage the receiving device 606 of the inner component 600 via the connector device 1412. In various embodiments, the connector device 1412 can be modified as necessary to removably engage a particular receiving device 606.

Figure 15:
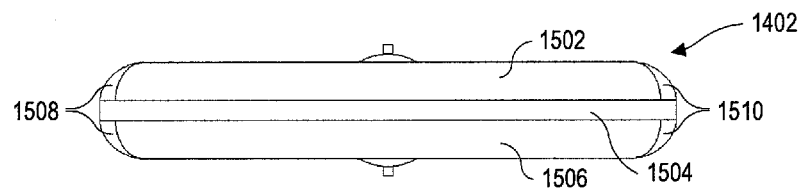
FIG. 15 illustrates a top view of the driver tool illustrated in FIG. 14.
Figure 16:
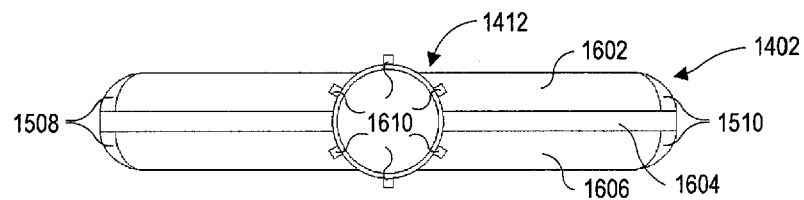
FIG. 16 illustrates a bottom view of the driver tool illustrated in FIG. 14.

FIGS. 15 and 16 illustrate top and bottom views, respectively, of the driver tool 1400 illustrated in FIG. 14. A top portion of the handle 1402 includes arcuate surfaces 1502, 1504, 1506, 1508 and 1510, while a bottom portion of the handle 1402 includes arcuate surfaces 1602, 1604, 1606, 1608 and 1610. In one embodiment illustrated in FIG. 16, the terminal body 1410 is tubular and the connector device 1412 includes connectors or extensions 1610 that can be received by the notches 607 of the receiving device 606 of the inner component 600.

Figure 17:
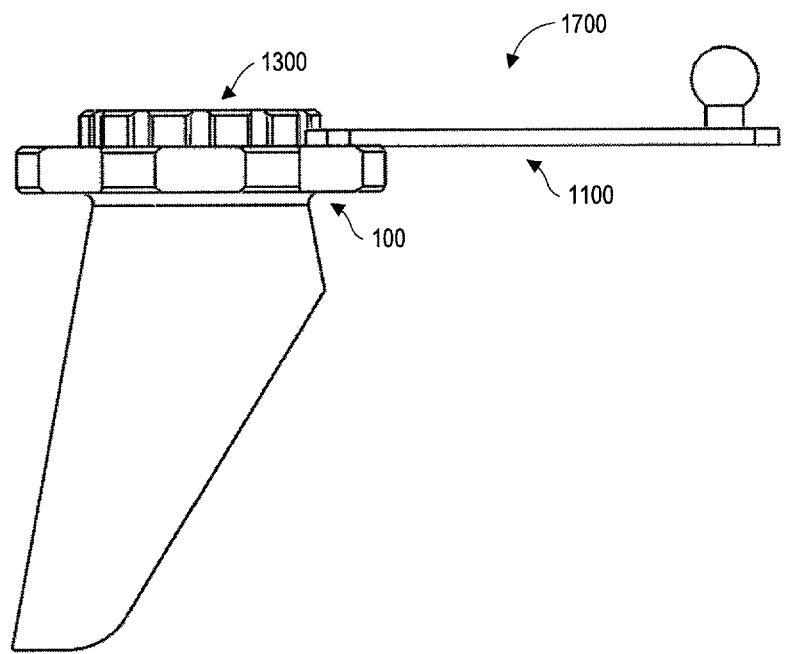
FIG. 17 illustrates a side view of an example minimally invasive surgical retractor with expanded field of vision according to the first embodiment.

FIG. 17 illustrates a side view of an example minimally invasive surgical retractor with expanded field of vision 1700 according to the first embodiment. The retractor 1700 is illustrated in a first rotational (e.g., closed) configuration. In some embodiments, the retractor 1700 includes only the outer component 600 and inner component 600. In other embodiments, the retractor 1700 includes the outer component 100, inner component and support arm 1100. In various embodiments, the retractor 1700 can also include the nut 1300.

Figure 18:
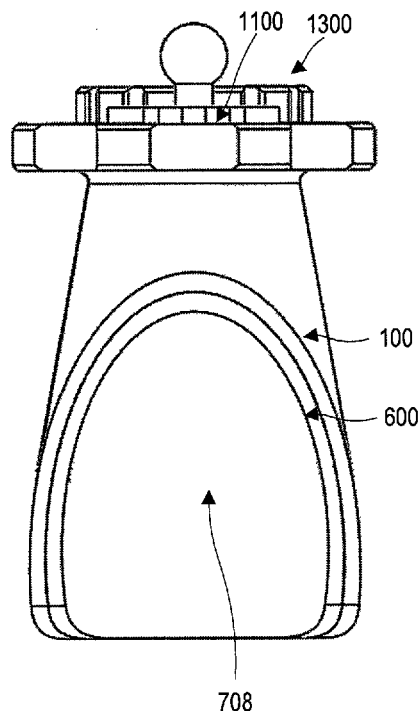
FIG. 18 illustrates a front view of the minimally invasive surgical retractor with expanded field of vision of FIG. 17.

FIG. 18 illustrates a front view of an example minimally invasive surgical retractor with expanded field of vision 1700 of FIG. 17. The inner component 600 is nested in the outer component 100 showing opening 708. In this first rotational configuration, the retractor 1700 can be inserted into a patient's wound or incision. As clearly illustrated in FIGS. 17 and 18, the refractor 1700 has improved minimally invasive characteristics because portions 309, 809 have been removed from the conical walls 114, 612 of the respective components 100, 600, as illustrated in greater detail in FIGS. 3 and 8, respectively.

Figure 19:
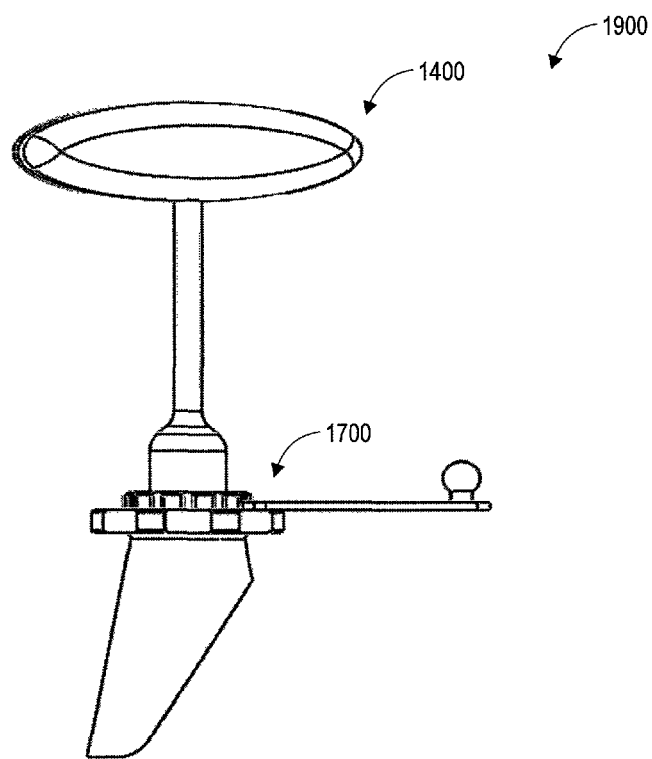
FIG. 19 illustrates a side view of an example minimally invasive surgical retractor system with the minimally invasive surgical retractor of FIG. 17 in a closed rotational configuration.

FIG. 19 illustrates a side view of an example minimally invasive surgical retractor system 1900 with the minimally invasive surgical retractor 1700 of FIG. 17 in a closed rotational configuration. The retractor system 1900 includes the minimally invasive surgical retractor 1700 of FIG. 17 and the driver tool 1400 of FIG. 14. The retractor 1700 is inserted into a wound or incision in a closed rotational configuration shown in FIG. 18. The nut 1300 is not tightened completely to allow components 100, 600 and support arm 1100 to rotate adjustably in relation to each other. In those embodiments where components 100, 600 and support arm 1100 are friction fit, the nut 1300 can be omitted completely.

After insertion, the driver tool 1400 is used to engage the inner component 600 and to adjustably rotate the inner component 600 with respect to the outer component 100. In one embodiment, the connectors 1610 of the connector device 1412 illustrated in FIG. 16 engage the notches 607 of the receiving device 606 illustrated in FIG. 9 to facilitate the rotation of the inner component 600 with respect to the outer component 100. After desired rotational adjustment, the nut 1300 can be used to fixate components 100, 600 and the support arm 1100 with respect to each other. In those embodiments where components 100, 600 and support arm 1100 are friction fit, the nut 1300 can also be used to provide additional fixation.

Figure 20:
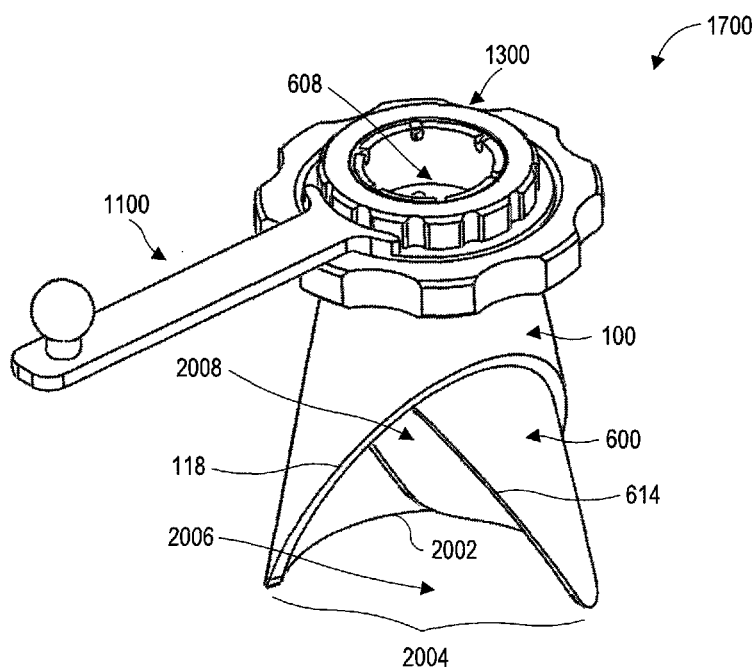
FIG. 20 illustrates a perspective view of the minimally invasive surgical retractor of FIG. 19 rotated to an intermediate rotational configuration.

FIG. 20 illustrates a perspective view of the minimally invasive surgical retractor 1700 of FIG. 19 rotated to an intermediate rotational configuration. There can be multiple intermediate rotational configurations. The driver tool 1400 is used to adjustably rotate the inner component 600 with respect to the outer component 100 into the intermediate rotational configuration. The nut 1300 can be tightened to secure or fixate components 100, 600 and support arm 1100 in relation to each other. Thereafter, the driver tool 1400 is removed. In the at least one intermediate rotational configuration of the components 100, 600, openings 208, 708 define a combined opening 2006 in communication with opening 608 of the inner component 600 that imparts or provides an expanded field of vision 2004 to the retractor 1700.

As illustrated in FIG. 20, in at least one intermediate rotational configuration, the outer component 100 and the inner component 600 are configured to form a continuous conical wall 2002 (e.g., without gaps between the components 100, 600) on one side and an open window 2008 defined by the intersection of walls 118, 614 on the other side. In certain instances such retraction can be desirable to provide access to the outside of the retractor 1700 via the window 2008 as well as to receive structures (or parts thereof) into combined opening 2006 of the retractor 1700 through the window 2008. The length of the conical wall 2002 and the size of the window 2008 can be adjusted by the rotational configuration of the inner component 600 with respect to the outer component 100. For example, during a spinal surgical procedure the retractor 1700 can be positioned much closer to the spinous midline process than is possible with conventional refractors. Specifically, the components 100, 600 can be rotationally adjusted with respect to one another to open a window 2008 that is appropriately sized and dimensioned such that at least a part of the spinous process can be received into the combined opening 2006 of the retractor 1700. This can improve the outcome of the surgical procedure.

In embodiments with peripheral light openings, at least one peripheral light opening 618 communicates with at least one peripheral light opening 106 in the multiple intermediate rotational configurations of the inner component 600 with respect to the outer component 100. In embodiments with translucent portions, the inner component 600 can be adjustably rotated with respect to the outer component 100 in a multiplicity of intermediate rotational configuration, as light can be communicated via the translucent portions of the components 100, 600. In the foregoing embodiments, the light emitted by portion 1204 of the light emitting device 1200 of FIG. 12 can be communicated via the peripheral light openings 106, 816 or via translucent portions to illuminate the combined opening 2006, providing sufficient lighting in the expanded field of vision 2102. Furthermore, sufficient lighting is also provided to the window 2008.

Figure 21:
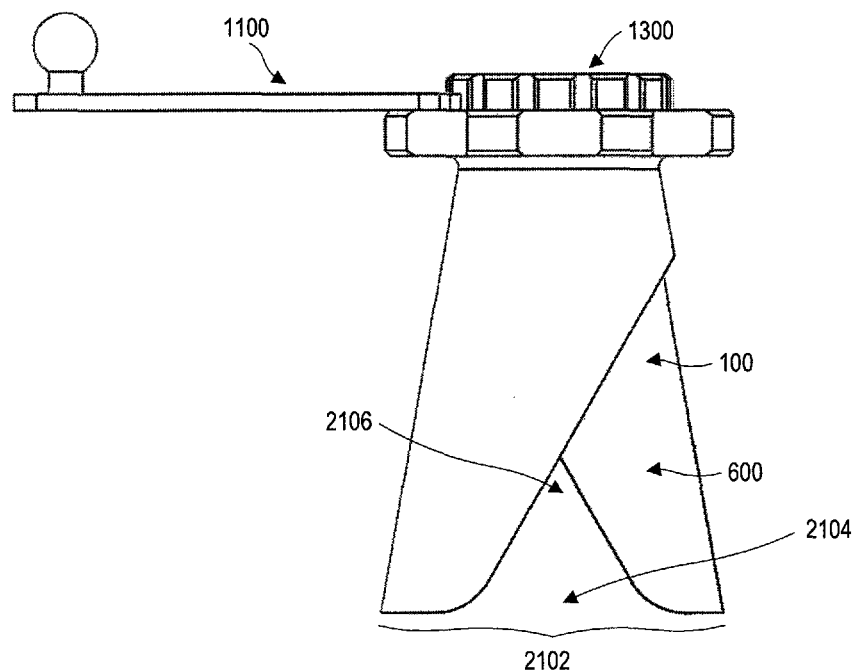
FIG. 21 illustrates a side view of the minimally invasive surgical retractor of FIG. 19 rotated to an open rotational configuration.

FIG. 21 illustrates a side view of the minimally invasive surgical retractor 1700 of FIG. 19 rotated to an open rotational configuration. In the open rotational configuration, the inner component 600 is rotated approximately 180 degrees from the closed configuration in relation to the outer component 100. In the open rotational configuration of the components 100, 600 illustrated in FIG. 21, the openings 207, 708 define a combined opening 2104 in communication with the opening 608 of the inner component 600 that imparts or provides an expanded field of vision 2102 to the refractor 1700. As further illustrated in FIG. 21, opposite windows 2106 formed by the intersection of the conical walls 114, 612 are small such that excellent refraction can be obtained from the surgical retractor 1700.

Figure 22:
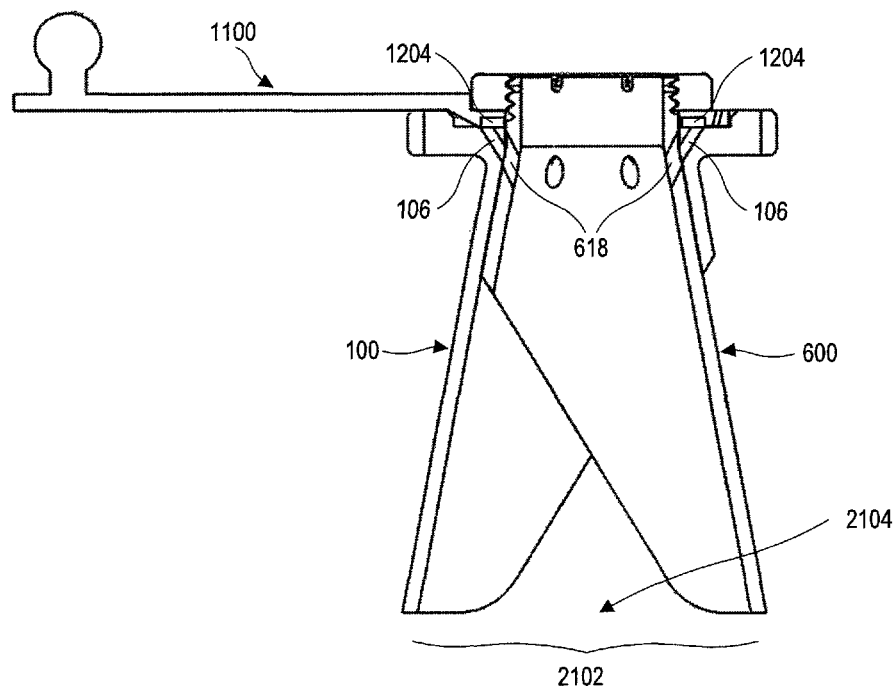
FIG. 22 illustrates a cross-sectional view of the minimally invasive surgical retractor of FIG. 21.

FIG. 22 illustrates a cross-sectional view of the minimally invasive surgical retractor 1700 of FIG. 21. In embodiments with peripheral light openings, at least one of the peripheral light openings 106 of the outer component 100 is in communication with at least one of the peripheral light openings 618 of the inner component 600. The light emitted by portion 1204 of the light emitting device 1200 is communicated through the peripheral light openings 106, 618 to illuminate the combined opening 2104, providing sufficient lighting in the expanded field of vision 2102. In embodiments with translucent portions of components 100, 600, the light emitted by portion 1204 of the light emitting device 1200 can be communicated via the translucent portions illuminating the conical walls 114, 612 of the respective components 100, 600 which in turn illuminate the combined opening 2104.

With reference to first embodiment of FIGS. 1-22, the minimally invasive surgical retractor can also include one or more additional components, similar to the inner component 600. In one example, a third innermost component can be inserted into the inner component 600 and can further be configured to be disposed adjustably in one or more rotational configurations with respect to the inner component 600. In some embodiments, the configuration and engagement of the third innermost can be similar to the configuration and engagement of inner component 600. In other embodiments, a top structure of the third innermost component can be provided with at least one slot transverse to its thread (e.g., transverse slot) that can enable the top structure to be squeezed, reducing its diameter to be fractionally smaller than the diameter of the opening 608 of structure 602 of component 600, such that the top structure of the innermost component can be disposed at least partially within the structure 602 of the inner component 600 and the innermost component can be rotationally configured with respect to the components 100, 600.

Figure 23:
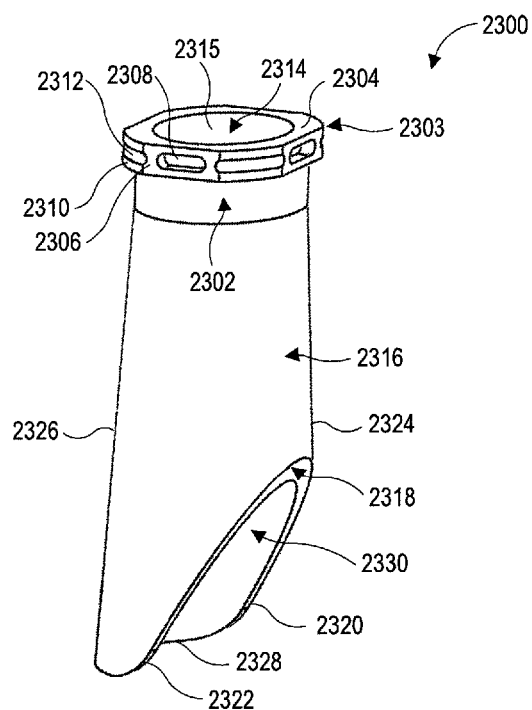
FIG. 23 illustrates a perspective view of an example outer component of a minimally invasive surgical retractor with expanded field of vision according to a second embodiment.
Figure 24:
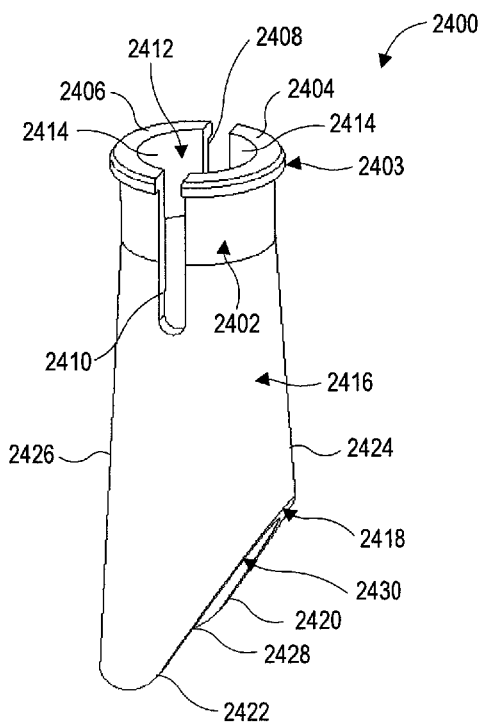
FIG. 24 illustrates a perspective view of an example inner component of the minimally invasive surgical retractor with expanded field of vision according to the first embodiment.

FIG. 23 illustrates a perspective view of an example outer component 2300 of a minimally invasive surgical retractor with expanded field of vision according to a second embodiment. The minimally invasive surgical retractor and its operation are illustrated in and described with reference to FIGS. 26-30 below. The outer component 2300 is configured to mate adjustably in a first rotational configuration (e.g., closed configuration) with respect to an example inner component (illustrated in FIG. 24). The outer component 2300 is also configured to rotate adjustably to a second rotational configuration (e.g., open configuration) with respect to the inner component of FIG. 24, and to secure rigidly in at least one of the rotational configurations. In various embodiments, one or more additional rotational configurations of the outer component 2300 with respect to the inner component of FIG. 24 are possible. The outer component 2300 is further configured to mate in one or more rotational configurations with a support arm (illustrated in FIG. 25).

The outer component 2300 includes an example top ring structure 2302 and an example bottom cone-shaped (conical) outer wall 2316. The ring structure 2302 is configured to facilitate handling and manipulation of the outer component 2300 and the assembled retractor, as illustrated in FIGS. 26-30. The ring structure 2302 includes a retaining member 2303 and a seat member 2304. The seat member 2304 is configured to mate with (or to receive) the inner component of FIG. 24. The seat member 2304 of the ring structure 2302 defines a plane. In one embodiment, the plane can be substantially horizontal.

The retaining member 2303 is configured to retain the minimally invasive surgical retractor outside a wound/incision during surgery and further configured to provide the ability to grasp the outer component 2300 for insertion and extraction of the minimally invasive surgical retractor with respect to the incision and for rotation of the outer component 2300 with respect the inner component of FIG. 24. The retaining member 2303 is further configured secure the support arm of FIG. 25.

The retaining member 2303 includes a plurality of peripheral surfaces 2306, 2310 and a central opening 2314, which is bounded by a cylindrically-shaped (cylindrical) inner wall 2315. The cylindrical inner wall 2315 extends from plane defined by the seat member 2304 substantially downwardly to the conical outer wall 2316. In some embodiments, the peripheral surfaces 2306, 2310 alternate. The peripheral surfaces 2306, 2310 extend substantially downwardly with respect to the plane defined by the seat member 2304 and facilitate grasping, holding and rotating.

The peripheral surfaces 2306 are generally planar and include peripheral slots 2308 configured to mate with reciprocal connectors of the support arm described below in reference to FIG. 25. Four (4) peripheral slots 2308 can be disposed equidistantly about the periphery of the retaining member 2303. More or fewer peripheral slots 2308 can be provided and the peripheral slots 2308 can be disposed at various locations about the periphery of the retaining member 2303. In some embodiments the peripheral slots 2308 can be open to and in communication with the central opening 2314 to provide peripheral light openings as described in greater detail below. In alternate embodiments, the peripheral slots 2308 can be closed and the inner wall 2315 translucent for communication with the central opening 2314 to provide the peripheral light openings.

The peripheral surfaces 2310 are generally curvilinear or arcuate and can include slots 2312. The slots can be configured as additional/alternate peripheral light openings described below or can be omitted.

The conical outer wall 2316 is configured to provide for minimally invasive insertion while expanding the field of vision, as will be described in greater detail below. The conical outer wall 2316 extends down and away from the ring structure 2303, forming an acute angle (e.g., angle <90 degrees) with respect to the plane defined by the seat member 2304. The conical wall 2316 is defined by a first side 2324, a second side 2326, and an oval-shaped (or ellipse-shaped) arch 2318 that extends from the first side 2324 to the second side 2326 toward an arcuate bottom 2328. The arch 2318 includes arcuate walls 2320, 2322 that are in communication with the bottom 2328. In one embodiment, the arcuate walls 2320, 2322 of the arch 2318 connect to the arcuate bottom 2328 via taper sections to form a smooth transition between the arch 2318 and the bottom 2328. The arch 2318 and the bottom 2328 form an opening 2330, which is in communication with the opening 2314 and through which the inner component of FIG. 24 is received. The formation of the conical outer wall 2316 can be similar to or different than the formation of the conical outer wall according to the first embodiment described with reference to FIG. 3 hereinabove.

The outer component 2300 can be made of a radiolucent plastic material (e.g., producing low artefact on an x-ray) another material, or a combination of materials. For example, the following materials and combinations thereof can be used: plastic, acrylic, polyether-ether-ketone (e.g., PEEK), carbon fiber, and metal. Other medically/surgically appropriate materials that have not been enumerated herein can also be used. In some embodiments, the entire outer component 2300 can be opaque or translucent. In alternate embodiments, one or more portions of the outer component 2300 can be translucent to transmit light. For example, the retaining member 2303 can be opaque, while the cylindrical inner wall 2315 and the conical outer wall 2316 can be translucent.

FIG. 24 illustrates a perspective view of an example inner component 2400 of the minimally invasive surgical retractor with expanded field of vision according to the second embodiment. As described above with reference to FIG. 23, the minimally invasive surgical retractor and its operation are illustrated in and described with reference to FIGS. 26-30 below. The inner component 2400 is configured to be disposed adjustably in a first rotational configuration (e.g., closed configuration) with respect to the example outer component 2300 of FIG. 23. The inner component 2400 is further configured to rotate adjustably to a second rotational configuration (e.g., open configuration) with respect to the outer component 2300, and to be secured in at least one of the rotational configurations with respect to the outer component 2300. In various embodiments, one or more additional rotational configurations of the inner component 2400 with respect to the outer component 2400 are possible.

The inner component 2400 includes an example top interlocking structure 2402 and an example bottom cone-shaped (conical) inner wall 2416. The top interlocking structure 2402 of the inner component 2400 is configured to be received or disposed at least partially inside the ring structure 2302 of the outer component 2300 of FIG. 23, e.g., via openings 2330 and 2314, such that the inner component 2400 can be rotationally adjustable from the first rotational configuration with respect to the outer component 2300 to the second rotational configuration with respect to the outer component 2300. The top interlocking structure 2402 includes deflectable lip members 2404, 2406, channels 2408, 2410 and a central opening 2412. The lip members 2404, 2406 of the top interlocking structure 2402 define a plane. In one embodiment, the plane can be substantially horizontal.

The deflectable lip members 2404, 2406 are separated by the channels 2408, 2410 and bound the central opening 2412. The channels 2408, 2410 bisect the interlocking structure 2402, extending substantially downwardly below the plane defined by the lip members 2404, 2406. In some embodiments, the channels 2408, 2410 extend at least partially down the interlocking structure 2402. In alternate embodiments, the channels 2408, 2410 can extend down the entirety of the interlocking structure 2402 and can continue at least partially down the conical inner wall 2416. The channels 2408, 2410 are sized and dimensioned to provide sufficient deflection of the lip members 2404, 2406 toward the center of the opening 2412 such that the top interlocking structure 2402 of the inner component 2400 can be received or disposed at least partially inside the ring structure 2302 of the outer component 2300 of FIG. 23.

Although only two (2) lip members 2404, 2406 separated by two (2) channels 2408, 2410 are shown, at least one of the lip members 2404, 2406 can further be separated by one or more additional channels (not shown). In some embodiments, four (4) lip members separated by four (4) channels can be disposed about the top interlocking structure 2402. These lip members can be equidistantly disposed about the top interlocking structure 2402.

As mentioned above, the lip members 2404, 2406 are deflectable toward a center of the opening 2412 such that the top interlocking structure 2402 of the inner component 2400 can be received into the outer component 2300 through the openings 2330, 2314. Specifically, as the inner component 2400 is advanced through the openings 2330, 2314, the lip members 2404, 2406 are incrementally deflected toward the center of the opening 2412 as the inner component 2400 travels along the interior of the conical outer wall 2316 and the interior of the cylindrical inner wall 2315 of the ring structure 2302 of FIG. 23. Once received, the lip members 2404, 2406 deflect back to their original positions and become disposed on or engage the seat member 2304 to secure the inner component 2400 with respect to the outer component 2300 from withdrawal via the lip members 2404, 2406 and from rotation by friction fitting of the interlocking structure 2402 within the ring structure 2303 and the inner wall 2416 within the outer wall 2316.

The channels 2408, 2410 are configured to provide for sufficient deflection of the lip members 2404, 2406 such that the inner component 2400 can be received into the outer component 2300 and also to provide sufficient friction-based engagement or securing of the inner component 2400 with respect to the outer component 2300. The channels 2408, 2410 are further configured to engage a driver tool (illustrated in FIG. 25) for rotational adjustability of the inner component 2400 with respect to the outer component 2300, as described in greater detail below with reference to FIGS. 27, 28. The central opening 2412 is bounded by a pair of cylindrically-shaped (cylindrical) inner walls 2414.

The conical inner wall 2416 is configured to provide for minimally invasive insertion while expanding the field of vision, as will be described in greater detail below. The conical outer wall 2416 extends down and away from the top interlocking structure 2402, forming an acute angle (e.g., angle <90 degrees) with respect to the plane defined by the lip members 2404, 2406. The conical wall 2416 is defined by a first side 2424, a second side 2426, and an oval-shaped (or ellipse-shaped) arch 2418 that extends from the first side 2424 to the second side 2426 toward an arcuate bottom 2428. The arch 2418 includes arcuate walls 2420, 2422 that are in communication with the bottom 2428. In one embodiment, the arcuate walls 2420, 2422 of the arch 2418 connect to the arcuate bottom 2428 via taper sections to form a smooth transition between the arch 2418 and the bottom 2428. The arch 2418 and the bottom 2428 form an opening 2430, which is in communication with the opening 2412. The formation of the conical inner wall 2416 can be similar to or different than the formation of the conical inner wall according to the first embodiment described with reference to FIG. 8 hereinabove.

The inner component 2400 can be made of a radiolucent plastic material, (e.g., producing low artefact on an x-ray), another material, or a combination of materials. For example, the following materials and combinations thereof can be used: plastic, acrylic, polyether-ether-ketone (e.g., PEEK), carbon fiber, and metal. Other medically/surgically appropriate materials that have not been enumerated herein can also be used. In some embodiments, the entire inner component 2400 can be opaque or translucent. In alternate embodiments, one or more portions of the inner component 2400 can be translucent. For example, the lip members 2404, 2406 can be opaque, cylindrical walls 2414 of the interlocking structure 2402 and the conical inner wall 2416 (or portion thereof) can be translucent.

In some alternate embodiments, the interlocking structure 2402 can include peripheral light openings (not shown) that are disposed about the interlocking structure 2402 and extend through the interlocking structure 2402 to the interior of the inner component 2400. In one embodiment, the peripheral light openings can be equidistantly disposed about the interlocking structure 2402. In another embodiment, the peripheral light openings can be disposed at various locations about the interlocking structure 2402. In the alternate embodiments, at least one peripheral light opening of inner component 2400 is in communication with at least one peripheral light opening 2308 of outer component 2300, in one or more rotational configurations of the inner component 2400 with respect to the outer component 2300.

Figure 25:
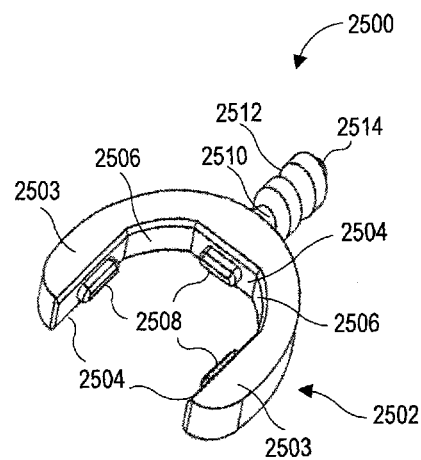
FIG. 25 illustrates a perspective view of an example support arm of the minimally invasive surgical retractor with expanded field of vision according to the second embodiment.

FIG. 25 illustrates a perspective view of an example support arm 2500 of the minimally invasive surgical retractor with expanded field of vision according to the second embodiment. The support arm 2500 is configured to mount or rigidly secure the minimally invasive surgical retractor to an external support structure of an operating table (not shown). Once the surgical retractor is in a desired position, multiple joints of the external support structure are locked to fixate the surgical retractor position and orientation in relation to the operating table and the patient. The example support arm 2500 includes a retractor attachment device 2502, a handle 2510 and a support attachment device 2512.

The retractor attachment device 2502 is configured to mate in one or more rotational configurations with respect to the outer component 2300 and inner component 2400 of FIGS. 23, 24, respectively. The retractor attachment device 2502 approximates a c-shape and includes distal extensions (or arms) 2503. The retractor attachment device 2502 further includes planar surfaces 2504, curvilinear surfaces 2506 and connectors 2508. The distal extensions 2503 are configured to be deflectable away from one another such that the connectors 2508 can engage the reciprocal slots 2308 of the ring structure 2302. The planar surfaces 2504 are configured to be disposed against the planar surfaces 2306 of the outer component 2300, and the curvilinear surfaces 2506 disposed against the curvilinear surfaces 2310 of the outer component 2300.

Once the connectors 2508 are engaged, the extensions 2503 are further configured to return to their un-deflected positions such that the support arm 2500 is rigidly secured to the outer component 2300. The support arm 2500 can be rotationally adjusted to various rotational configurations with respect to the outer component 2300 and the inner component 2400 by disengaging the connectors 2508, rotating the support arm in relation to the outer component 2300, and re-engaging the connectors 2508 with the reciprocal slots 2308 of the ring structure 2302.

The handle 2510 extends from the retractor attachment device 2502 and is configured to facilitate the positioning and engagement of the retractor attachment device 2502 in one or more rotational configurations with respect to the outer component 2300 and the inner component 2400 of FIGS. 23 and 24, respectively. The support attachment device 2512 extends from a terminal end of the handle 2510 and is configured to secure to an external support structure described above. In one embodiment, the support attachment device 2512 can be a grooved cylindrical structure that is engaged by a receiver device (not shown) of the external support structure. The receiver device and the attachment device 2512 can be locked in desired position to fixate the surgical retractor as described above.

The example support arm 2500 can include a light emitting device 2514. The light emitting device 2514 can be a fiber optic cable or fiber connected to a light source (not shown). In some embodiments, the light emitting device 2514 can be embedded in the handle 2510 and refractor attachment device 2502, and exposed to emit light via connectors 2508 through peripheral light openings 2308 into the expanded field of vision defined by the components 2300, 2400, as described in greater detail below with reference to FIG. 30. In additional or alternate embodiments, the light emitting device 2514 can also be exposed to emit light via planar and curvilinear surfaces 2504, 2506 to respective surfaces 2306, 2310 into the expanded field of vision defined by the components 2300, 2400, as will be described in greater detail below with reference to FIGS. 29 and 30.

Figure 26:
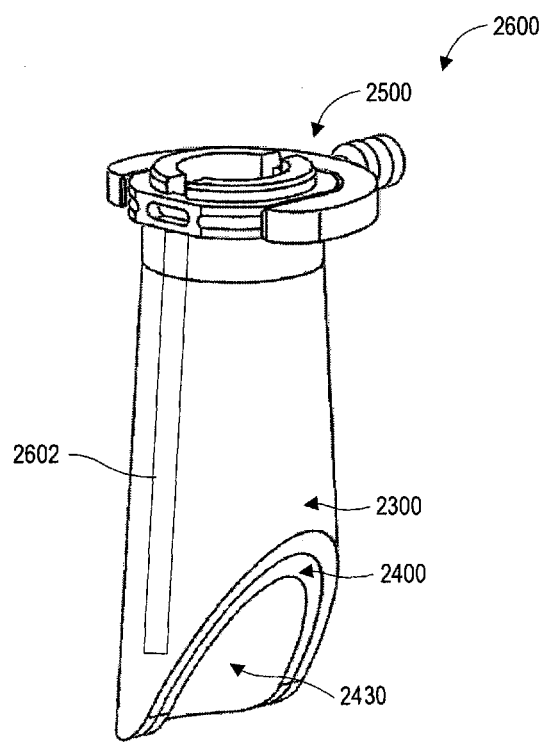
FIG. 26 illustrates a perspective view of an example minimally invasive surgical retractor with expanded field of vision according to the second embodiment.

FIG. 26 illustrates a perspective view of an example minimally invasive surgical retractor with expanded field of vision 2600 according to the second embodiment. In some embodiments, the retractor 2600 includes only the outer component 2300 and inner component 2400. In other embodiments, the retractor 2600 includes the outer component 2300, inner component 2400 and support arm 2500. The retractor 2600 is illustrated in a first rotational configuration (e.g., closed configuration) showing opening 2430. In this first rotational configuration, the retractor 2600 is in a minimally invasive configuration for insertion into a patient's wound/incision. As illustrated in FIG. 26, the retractor 2600 has an improved minimally invasive characteristic as characterized by the oval-shaped (or ellipse-shaped) arches 2318, 2418 of the respective conical walls 2316, 2416. As described herein, portions removed from the conical walls 2316, 2416 of the respective components 2300, 2400 define the respective arches 2318, 2418.

As illustrated in FIG. 26, in addition to or alternatively to the other light emitting devices described herein, one or more light strips 2602 can be disposed on or at least partially embedded in at various locations of the outer component 2300, providing light into the expanded field of vision defined by the components 2300, 2400 of the retractor 2600, as will be described in greater detail below with reference to FIGS. 29 and 30. For example, one of the light strips 2602 can be disposed on or at least partially embedded in at least a portion of the conical outer wall 2316 of the outer component 2300.

Figure 27:
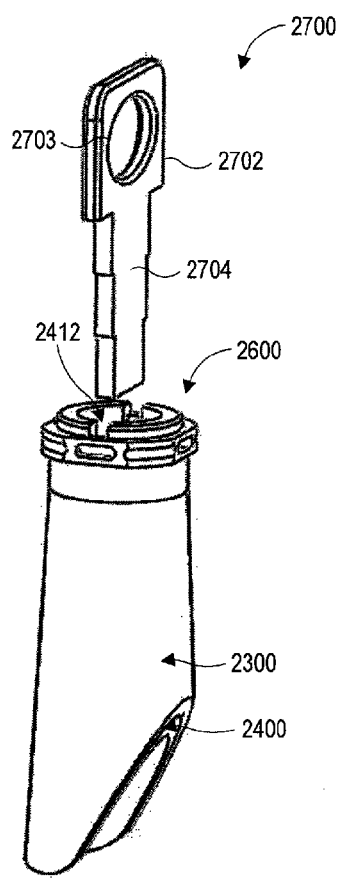
FIG. 27 illustrates a side view of an example minimally invasive surgical retractor system with the minimally invasive surgical retractor of FIG. 26 in the closed rotational configuration.

FIG. 27 illustrates a perspective view of an example minimally invasive surgical retractor system with the minimally invasive surgical retractor 2600 of FIG. 26 in the closed rotational configuration. The refractor system includes the minimally invasive surgical retractor 2600 and a driver tool (e.g., key-shaped driver) 2700. The driver tool 2700 includes a head 2702 and an engagement body 2704. The head 2702 can include an opening 2703 that can be used to tether the driver tool 2700, preventing the driver tool 2700 from becoming lost during a surgical procedure. The engagement body 2704 is configured to be inserted at least partially into the opening 2412 of the inner component 2400 and to further configured to engage the channels 2408, 2410 of the inner component 2400.

After the retractor 2600 is inserted into a wound, the driver tool 2700 is used to engage the inner component 2400 and to adjustably rotate the inner component 2400 with respect to the outer component 2300. More specifically, the engagement body 2704 of the driver tool 2700 engages the channels 2408, 2410 of the inner component 2400 to facilitate the rotation of the inner component 2400 with respect to the outer component 2300. Although the components 2300, 2400 are friction-fit, they provide sufficient play to enable the driver tool to overcome the friction between the components 2300, 2400 in order to rotate of the inner component 2400 with respect to the outer component 2300.

Figure 28:
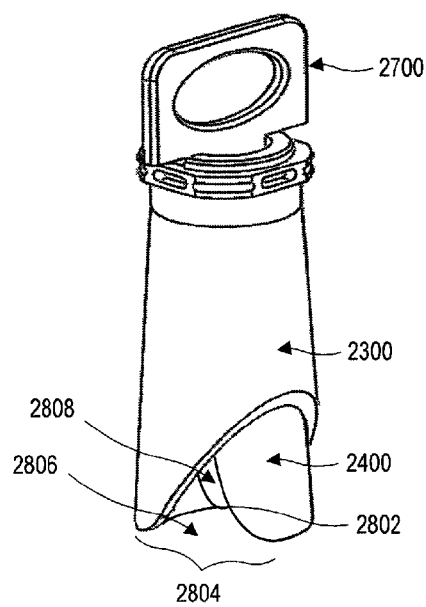
FIG. 28 illustrates a perspective view of the minimally invasive surgical retractor of FIG. 27 rotated to an intermediate rotational configuration.

FIG. 28 illustrates a perspective view of the minimally invasive surgical retractor 2600 of FIG. 26 rotated to an intermediate rotational configuration. There are multiple rotational configurations between a substantially closed configuration and a substantially open configuration. More specifically, the driver tool 2700 can be used to adjustably rotate the inner component 2400 with respect to the outer component 2300 to a desired intermediate rotational configuration. As the driver tool 2700 is removed, the components 2300, 2400 remain in the desired configuration by friction-fitting.

As illustrated in FIG. 28, in at least one intermediate rotational configuration, the outer component 2300 and the inner component 2400 are configured to form a continuous conical wall 2802 (e.g., without gaps between the components 2300, 2400) on one side and an open window 2808 defined by the intersection of walls 2322, 2420 on the other side. In certain instances such retraction can be desirable to provide access to the outside of the retractor 2600 via the window 2808, as well as to receive structures (or parts thereof) into the combined opening 2006 of the retractor 1700 through the window 2008. The length of the conical wall 2802 and the size of the window 2808 can be adjusted by the rotational configuration of the inner component 2400 with respect to the outer component 2300.

In the at least one intermediate rotational configuration of the components 2300, 2400, openings 2332, 2430 define a combined opening 2806 in communication with opening 2412 of the inner component 2400 that imparts or provides an expanded field of vision 2804 to the retractor 2600. Light emitted by the light emitting device 2514 of support arm 2500 illustrated in FIG. 25 and/or the light strip(s) 2602 illuminates the combined opening 2806, providing sufficient lighting in the expanded field of vision 2804. Furthermore, sufficient lighting is also provided to the window 2808.

Figure 29:
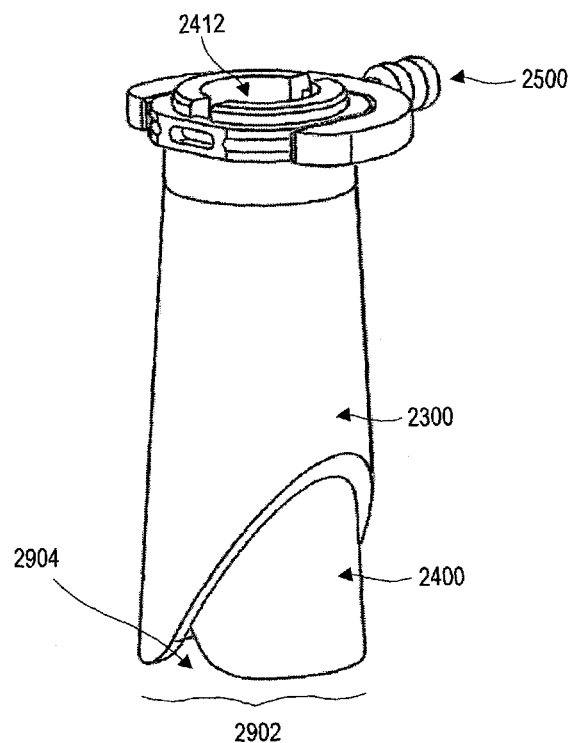
FIG. 29 illustrates a perspective view of the minimally invasive surgical retractor of FIG. 27 rotated to an open rotational configuration.

FIG. 29 illustrates a perspective view of the minimally invasive surgical retractor 2600 of FIG. 26 in an open rotational configuration. In the open rotational configuration, the inner component 2400 is rotated approximately 180 degrees from the closed configuration in relation to the outer component 2300. In the open rotational configuration of the components 2300, 2400 illustrated in FIG. 29, the openings 2330, 2430 define a combined opening 2904 in communication with the opening 2412 of the inner component 2400 that imparts or provides an expanded field of vision 2902 to the retractor 2600. As further illustrated in FIG. 29, opposite windows formed by the intersection of the conical walls 2316, 2416 are small such that excellent retraction can be obtained from the surgical retractor 2600.

Figure 30:
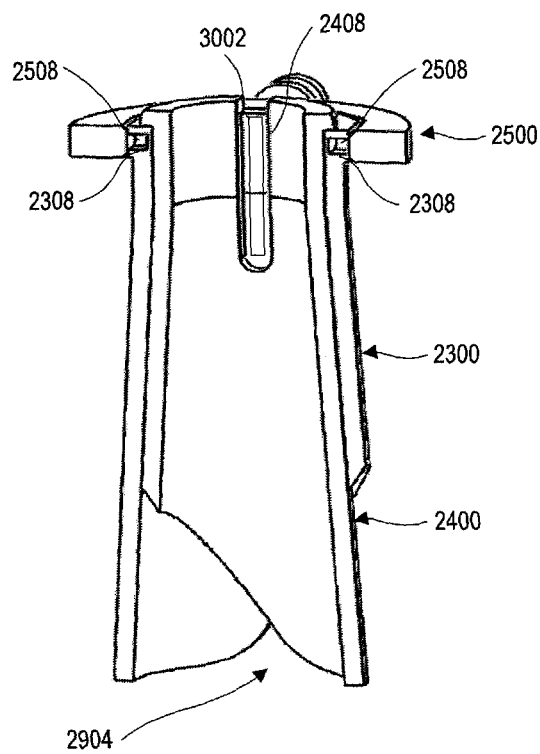
FIG. 30 illustrates a cross-sectional view of the minimally invasive surgical retractor of FIG. 29.

FIG. 30 illustrates a cross-sectional view of the minimally invasive surgical retractor 2600 of FIG. 29. In the open rotational configuration, the inner component 2400 is rotated approximately 180 degrees from the closed configuration in relation to the outer component 2300. In embodiments with translucent conical walls 2300, 2400, the light emitted via the connectors 2508 and/or surfaces 2504, 2506 of the support 2500, and/or one or more lights strips 2602 of outer wall 2300, illuminates the translucent conical walls 2316, 2416 of the respective components 2300, 2400, which in turn illuminate the combined opening 2904, providing sufficient lighting in the expanded field of visions 2902, and further to illuminate the window 2808. In additional or alternate embodiments, a light strip 3002 can be removably disposed in the channel 2408. Similarly a light strip (not shown) can also be removably disposed in the opposite channel 2410, illustrated in FIG. 24.

In embodiments with peripheral light openings in the components 2300, 2400, at least one of the peripheral light openings of the outer component 2300 is in communication with at least one of the peripheral light openings of the inner component 2400. The light emitted via at least one of the connectors 2508 or surfaces 2504, 2506 is communicated through the communicating peripheral light openings to illuminate the combined opening 2904, providing sufficient lighting in the expanded field of vision 2902, and further to illuminate the window 2808.

With reference to the second embodiment of FIGS. 23-20, the minimally invasive surgical retractor can also include one or more additional components, similar to the inner component 2400. In one example, a third innermost component can be inserted into the inner component 2400 and can further be configured to be disposed adjustably in one or more rotational configurations with respect to the inner component 2400. In such embodiments, the configuration and engagement of the third innermost component can be similar to the configuration and engagement of inner component 2400. The staggered engagement body 2704 of driver tool 2700 can be used to successively rotate the inner component 2400, followed by the innermost component. More specifically, advancing the driver tool 2700 to a first engagement position deepest in the opening 2412 can engage a widest portion of the engagement body 2704 with the channels of the innermost component and the channels 2408, 2410 inner component 2400. Thereafter, the driver tool 2700 can be withdrawn to a second engagement position shallower in the opening 2412 such that a narrower portion of the engagement body 2704 can engage the channels 2408, 2410 of the inner component 2400 and not the channels of the innermost component. Accordingly, the described components can be rotationally adjusted into desired rotational configuration with respect to each other.

In accordance with FIGS. 1-30, the minimally invasive surgical refractor can be used, among other medical/surgical procedures, in muscle sparing spinal surgery to reduce tissue trauma, decrease incision size and expand field of vision to improve the outcome of the surgical procedure. In operation, the minimally invasive surgical retractor can be inserted into a wound/incision in a first (closed) configuration and rotated into a second (partially or fully open) configuration. Light can be provided via the minimally invasive surgical retractor to illuminate the field of vision.

Thus, a minimally invasive surgical retractor and method of minimally invasive retraction that expand the field of vision have been described. Although specific example embodiments have been described, it will be evident that various modifications and changes can be made to these embodiments without departing from the broader scope of this application. Accordingly, the specification and drawings are to be regarded in an illustrative rather than a restrictive sense. The accompanying drawings that form a part hereof, show by way of illustration, and not of limitation, specific embodiments in which the subject matter can be practiced. The embodiments illustrated are described in sufficient detail to enable those skilled in the art to practice the teachings disclosed herein. Other embodiments can be utilized and derived therefrom, such that structural substitutions and changes can be made without departing from the scope of this application. This Detailed Description, therefore, is not to be taken in a limiting sense, and the scope of various embodiments is defined only by the appended claims, along with the full range of equivalents to which such claims are entitled.

Such embodiments of the inventive subject matter can be referred to herein, individually and/or collectively, by the term "invention" merely for convenience and without intending to voluntarily limit the scope of this application to any single invention, inventive concept or embodiment. Thus, although specific embodiments have been illustrated and described herein, it should be appreciated that any arrangement calculated to achieve the same purpose can be substituted for the specific embodiments shown. This application is intended to cover any and all adaptations or variations of various embodiments. Combinations of the above embodiments and other embodiments not specifically described herein, will be apparent to those of skill in the art upon reviewing the above description.

The Abstract is provided to comply with 37 C.F.R. §1.72(b) and will allow the reader to quickly ascertain the nature of the technical disclosure of this application. It is submitted with the understanding that it will not be used to interpret or limit the scope or meaning of the claims.

In the foregoing description of the embodiments, various features can be grouped together in a single embodiment for the purpose of streamlining the disclosure of this application. This method of disclosure is not to be interpreted as reflecting that the claimed embodiments have more features than are expressly recited in each claim. Rather, as the following claims reflect, inventive subject matter lies in less than all features of a single disclosed embodiment.

What is claimed is:

1. A surgical retractor comprising:
    a first component including a first top structure and a conical outer wall, the first top structure having a first opening, the conical outer wall extending below the first top structure to form an ellipse-shaped second opening in communication with the first opening;
    a second component including a second top structure and a conical inner wall, the second top structure having a third opening, the conical inner wall extending below the second top structure to form an ellipse-shaped fourth opening in communication with the third opening; and
    wherein the second top structure is disposed at least partially inside the first top structure such that the second component is rotatably adjustable with respect to the first component from a first rotational configuration to a second rotational configuration in which the ellipse-shaped second opening and the ellipse-shaped fourth opening define a combined opening that is in communication with the third opening to provide an expanded field of vision.

2. The surgical retractor of claim 1, wherein the first rotational configuration is a closed configuration and the second rotational configuration is between the closed configuration and an open configuration that is about 180 degrees with respect to the closed configuration.

3. The surgical retractor of claim 1, wherein the first rotational configuration is a closed configuration and the second rotational configuration is an open configuration at about 180 degrees with respect to the closed configuration.

4. The surgical retractor of claim 1, wherein the conical outer wall is defined by a truncated cone having a section removed, the section being defined from an offset along a first side of the truncated cone below the first top structure and extending down at an acute angle with respect to an axis of the truncated cone toward to an opposite side of the truncated cone.

5. The surgical retractor of claim 1, wherein the conical inner wall is defined by a truncated cone having a section removed, the section being defined from an offset along a first side of the truncated cone below the second top structure and extending down at an acute angle with respect to an axis of the truncated cone toward to an opposite side of the truncated cone.

6. The surgical retractor of claim 1, further comprising a support arm to mate with the first top structure in a rotational configuration.

7. The surgical retractor of claim 6, wherein the first top structure includes a recessed seat to receive the support arm.

8. The surgical retractor of claim 6, wherein the first top structure includes at least one peripheral slot to receive a reciprocal extension of the support arm.

9. The surgical retractor of claim 6, further comprising a nut to secure the second component via its second structure with respect to the first top structure of first component and the support arm in respective rotational configurations.

10. The surgical retractor of claim 6, wherein the support arm includes a light emitting device to emit light.

11. The surgical retractor of claim 10, wherein the first top structure of the first component includes at least one first peripheral light opening disposed about the first opening to communicate light emitted from the light emitting device of the support arm to the first opening.

12. The surgical retractor of claim 11, wherein the conical inner wall of the second component includes at least one second peripheral light opening disposed about the conical inner wall and in communication with the ellipse-shaped fourth opening, the at least one second peripheral light opening in communication with the at least one first peripheral light opening in the second rotational configuration to illuminate the combined opening.

13. The surgical retractor of claim 10, wherein the first top structure of the first component includes a first translucent portion disposed about the first opening to communicate light emitted from the light emitting device of the support arm to the conical outer wall, wherein at least a portion of the conical outer wall is translucent.

14. The surgical retractor of claim 13, wherein at least a portion of the conical inner wall is translucent and in communication with the first translucent portion of the first top structure.

15. The surgical retractor of claim 1, further comprising at least one light strip disposed on or at least partially embedded in at least a portion of the conical outer wall, the light strip configured to communicate light emitted by the light strip into the combined opening.

16. The surgical retractor of claim 1, wherein the second top structure of second component includes at least one channel extending transversely to the second top structure, the at least one channel sized and configured to allow the second top structure to be deflected such that the second top structure is enabled to be disposed at least partially inside the first top structure of the first component in a friction-fitted rotational configuration.

17. The surgical retractor of claim 16, further comprising at least one light strip removeably disposed in the at least one channel, the light strip configured to communicate light emitted by the light strip into the combined opening.

18. The surgical retractor of claim 1, wherein the second top structure of second component includes a plurality of lip members separated by at least one channel extending transversely to the second top structure, the at least one channel sized and configured to allow the lip members to deflect toward the center of the third opening such that the second top structure of the second component is enabled to be disposed at least partially inside the first top structure of the first component.

19. The surgical retractor of claim 1, wherein an intersection of the conical inner wall and the conical outer wall in the second rotational configuration defines a window providing access on a side of the surgical retractor such that a structure or a portion thereof is receivable into the combined opening.

20. A surgical retractor system comprising:
  a surgical retractor comprising:
    a first component including a first top structure and a conical outer wall, the first top structure having a first opening, the conical outer wall extending below the first top structure and forming an ellipse-shaped second opening in communication with the first opening;
    a second component including a second top structure and a conical inner wall, the top structure having a third opening, the conical inner wall extending below the second top structure to form an ellipse-shaped fourth opening in communication with the third opening, the second top structure being disposed at least partially inside the first top structure such that the second component is rotatably adjustable with respect to the first component; and
  a driver tool configured to engage the second top structure of the second component and to rotate the second component with respect to the first component from a first rotational configuration to a second rotational configuration in which the ellipse-shaped second opening and the ellipse-shaped fourth opening define a combined opening that is in communication with the third opening to provide an expanded field of vision.

21. The surgical retractor system of claim 20, wherein:
  the second top structure of the second component includes a plurality of notches; and
  the driver tool includes a plurality of connectors, each of the connectors engaging a respective notch such that the second component is rotatable with respect to the first component from the first rotational configuration to the second rotational configuration.

22. The surgical retractor system of claim 20, wherein:
  the second top structure of the second component includes opposing slots extending transversely to the second top structure; and
  the driver tool includes an elongated engagement body to engage the opposing slots such that the second component is rotatable with respect to the first component from the first rotational configuration to the second rotational configuration.

23. A method of retracting, the method comprising:
  inserting a surgical retractor in an incision of a patient, the surgical retractor including:
    a first component having a first top structure that includes a first opening, and a conical outer wall extending below the first top structure to form an ellipse-shaped second opening in communication with the first opening;
    a second component having a second top structure that includes a third opening, and a conical inner wall outer extending below the second top structure to form an ellipse-shaped fourth opening in communication with the third opening, the second top structure being disposed at least partially inside the first top structure in a first rotational configuration; and rotating the second component with respect to the first component from the first rotational configuration to a second rotational configuration in which the ellipse-shaped second opening and the ellipse-shaped fourth opening define a combined opening that is in communication with the third opening to provide an expanded field of vision.

24. The method of retracting of claim 23, further comprising securing a support arm to the first top structure in a rotational configuration with respect to the surgical retractor.

25. The method of retracting of claim 24, further comprising communicating light emitted from the support arm through at least one peripheral light opening of the first top structure in communication with at least one peripheral light opening of the conical inner wall to illuminate the combined opening.

26. The method of retracting of claim 24, further comprising communicating light emitted from the support arm through a translucent portion of the first top structure in communication with a translucent portion of the outer wall and a translucent portion of the inner wall to illuminate the combined opening.

27. The method of retracting of claim 23, further communicating light emitted from at least one light strip disposed on or at least partially embedded in at least a portion of the conical outer wall into the combined opening.

28. The method of retracting of claim 23, further comprising communicating light emitted from at least one light strip removeably disposed in at least one channel of the second top structure that extends transversely to the second top structure into the combined opening.

29. The method of retracting of claim 23, further comprising:

rotating the second component with respect to the first component from the second rotational configuration to the first rotational configuration; and withdrawing the surgical retractor from the incision of the patient.

* * * * *